(12) United States Patent
Herlitze et al.

(10) Patent No.: US 10,227,391 B2
(45) Date of Patent: Mar. 12, 2019

(54) SYSTEM AND METHOD FOR CONTROLLING G-PROTEIN COUPLED RECEPTOR PATHWAYS

(71) Applicant: CASE WESTERN RESERVE UNIVERSITY, Cleveland, OH (US)

(72) Inventors: Stefan Herlitze, Cleveland, OH (US); Lynn Landmesser, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 15/069,364

(22) Filed: Mar. 14, 2016

(65) Prior Publication Data

US 2016/0333069 A1 Nov. 17, 2016

Related U.S. Application Data

(63) Continuation-in-part of application No. 12/375,114, filed as application No. PCT/US2007/074439 on Jun. 26, 2007, now Pat. No. 9,284,363.

(60) Provisional application No. 60/833,378, filed on Jul. 26, 2006.

(51) Int. Cl.
  *C07K 14/705* (2006.01)
  *C07K 16/00* (2006.01)
  *C12N 5/079* (2010.01)
(52) U.S. Cl.
  CPC ...... *C07K 14/705* (2013.01); *C07K 14/70571* (2013.01); *C12N 5/0618* (2013.01); *C07K 2319/00* (2013.01); *C12N 2510/00* (2013.01)

(58) Field of Classification Search
  None
  See application file for complete search history.

(56) References Cited

U.S. PATENT DOCUMENTS

| | | | |
|---|---|---|---|
| 2003/0040080 A1 | 2/2003 | Miesenbock et al. | |
| 2005/0186658 A1 | 8/2005 | Gupta et al. | |
| 2007/0099263 A1 | 5/2007 | Milligan et al. | |
| 2008/0182811 A1* | 7/2008 | Ohsu | A61K 31/185 514/44 R |

OTHER PUBLICATIONS

Wyk et al., Restoring the ON Switch in Blind Retinas: Opto-mGluR6, a Next-Generation, Cell-Tailored Optogenetic Tool, May 7, 2015, PLoS biology vol. 13, No. 5, pp. e1002143, 30 pages.*
Kim et al., Light-Driven Activation of beta2-Adrenergic Receptor Signaling by a Chimeric Rhodopsin Containing the beta2-Adrenergic Receptor Cytoplasmic Loops, Feb. 22, 2005, Biochemistry 44(7):2284-2292.*
Yin et al., Probing Receptor Structure/Function with Chimeric G-Protein-Coupled Receptors, 2004, Molecular Pharmacology 65(6):1323-1332.*
Terakita, A., The opsins, Mar. 2005, Genome Biology 6:213, 9 pages.*

* cited by examiner

*Primary Examiner* — John D Ulm
(74) *Attorney, Agent, or Firm* — Tarolli, Sundheim, Covell & Tummino LLP

(57) ABSTRACT

A light-sensitive G-protein coupled receptor includes a light sensitive extracellular cone opsin or melanopsin domain and a hetorologous intracellular domain capable of modulating an intracellular signaling pathway.

10 Claims, 25 Drawing Sheets
Specification includes a Sequence Listing.

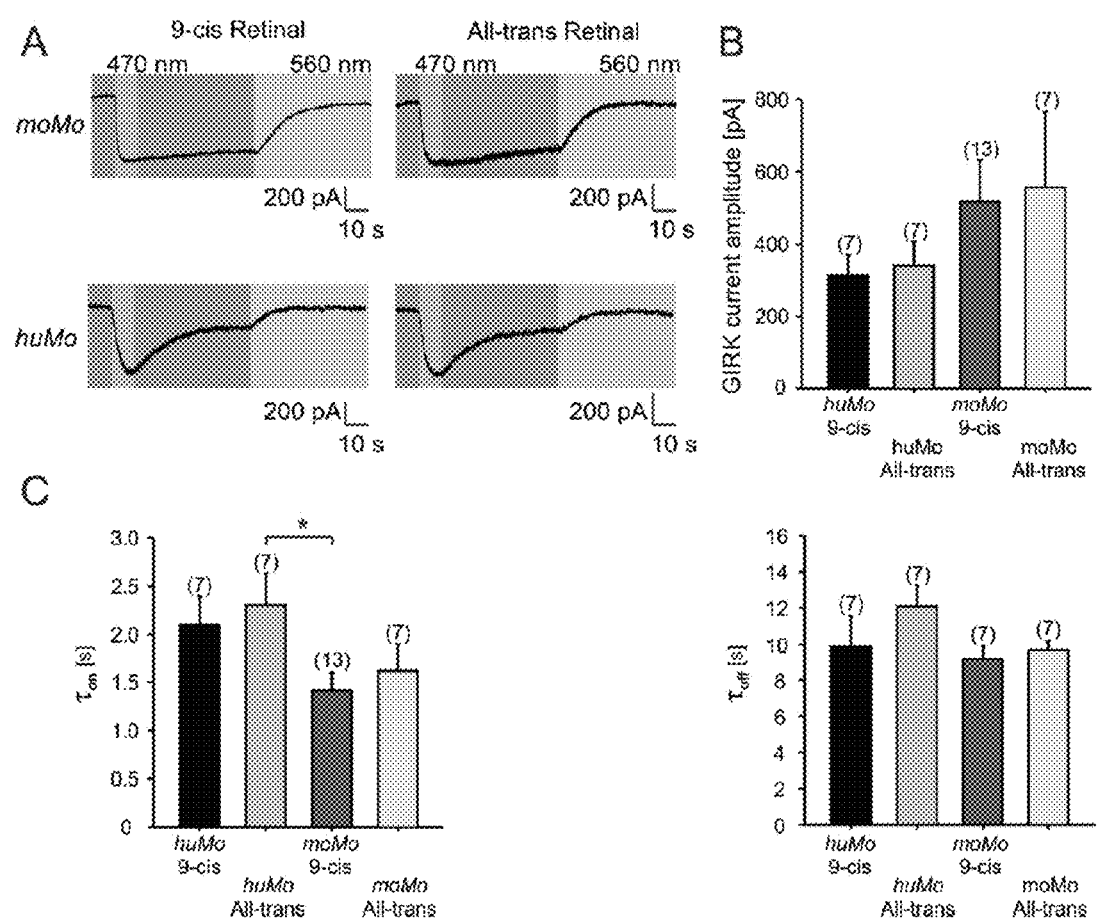
Figs. 9A-C

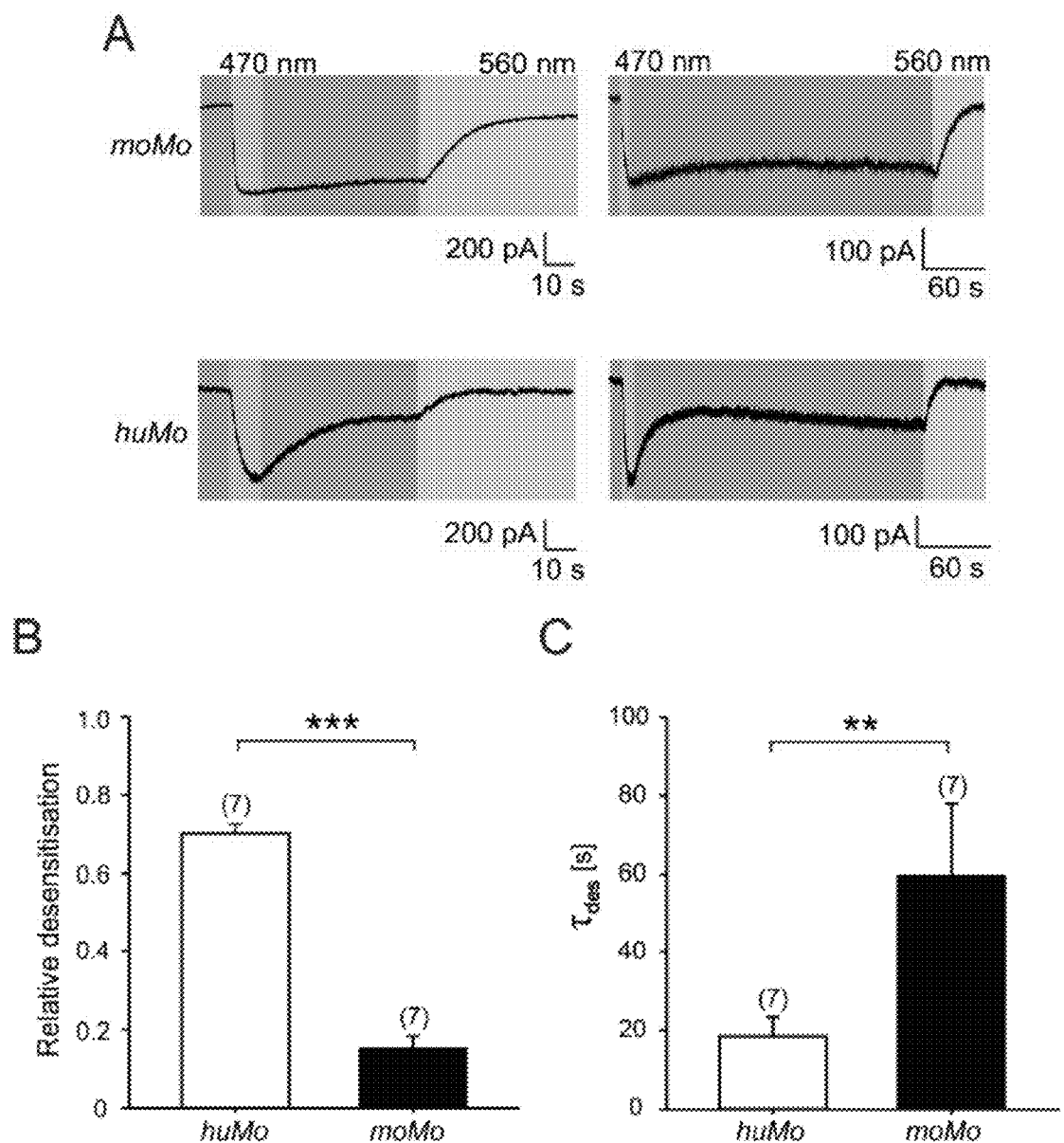
Figs. 10A-C

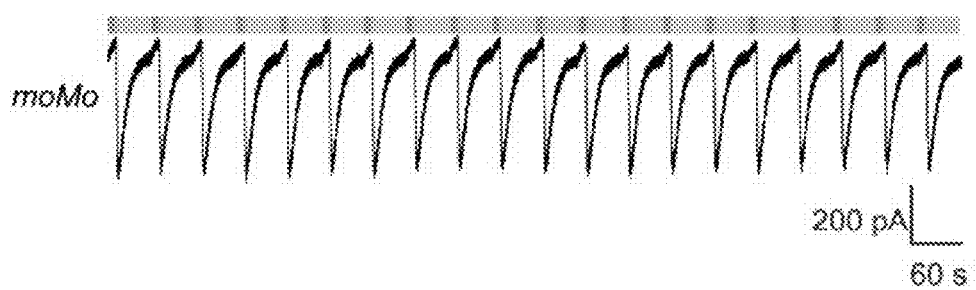
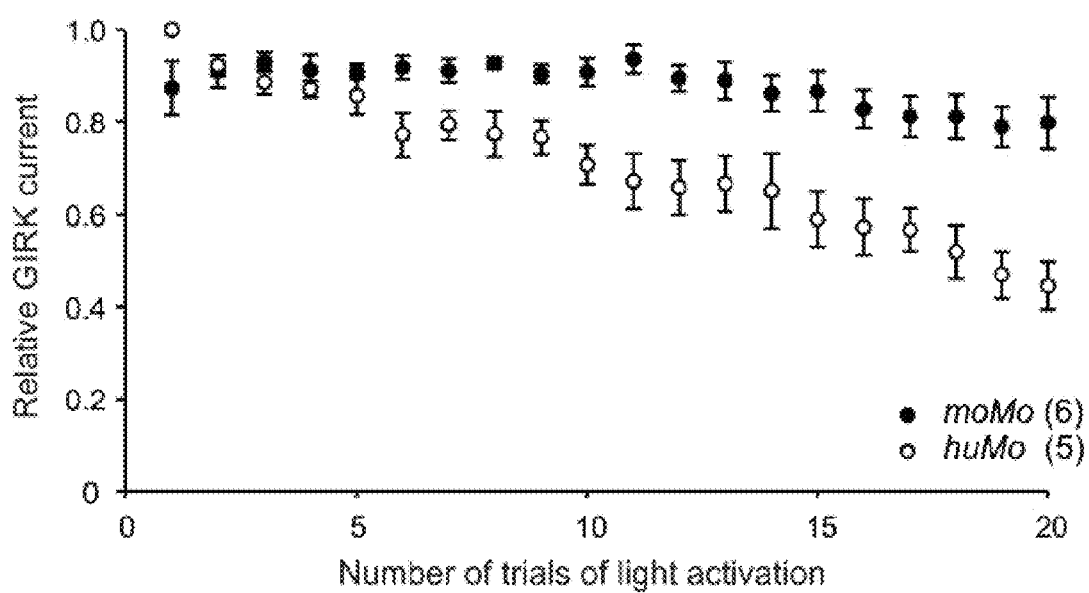
Figs. 10D-E

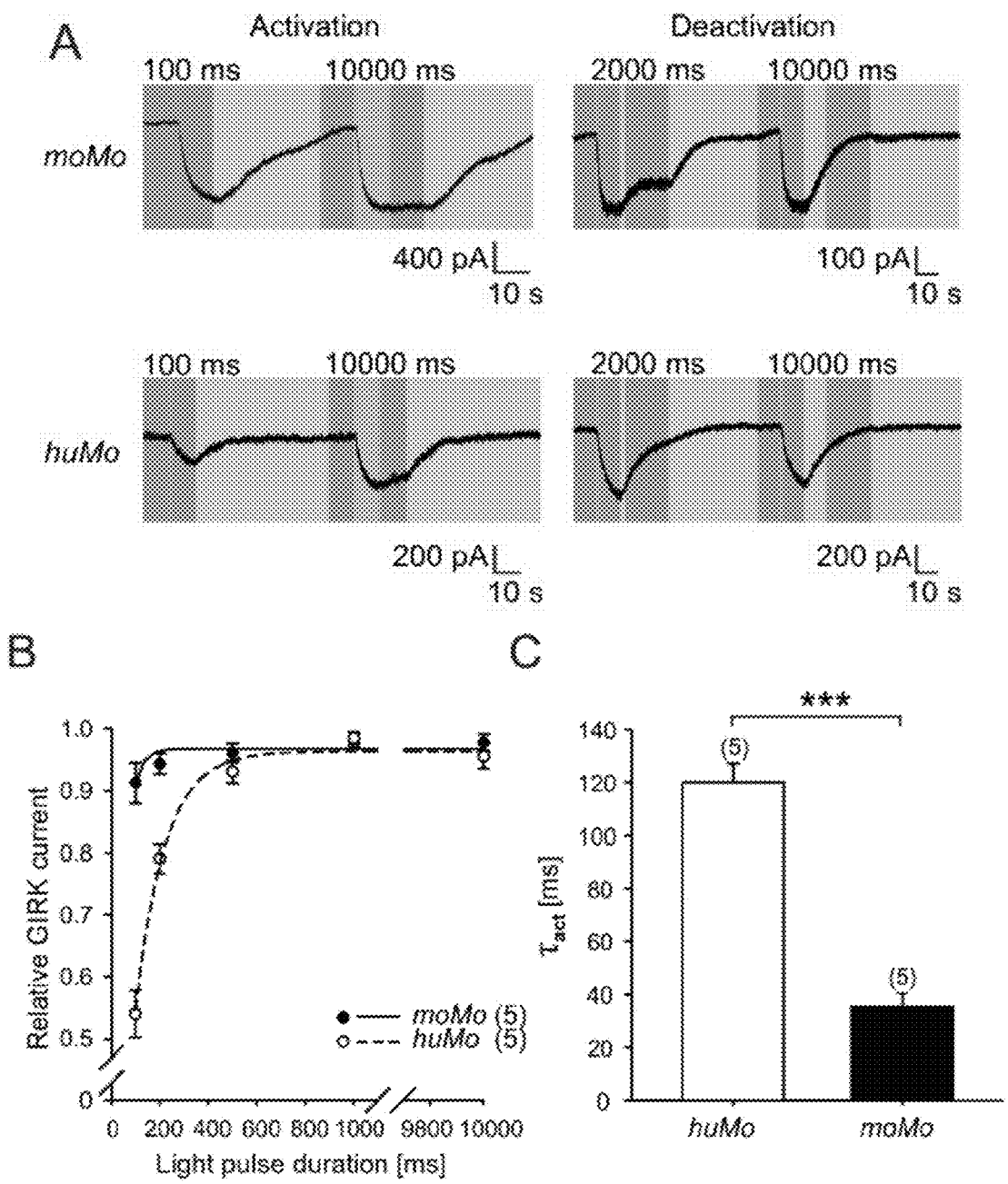
Figs. 11A-C

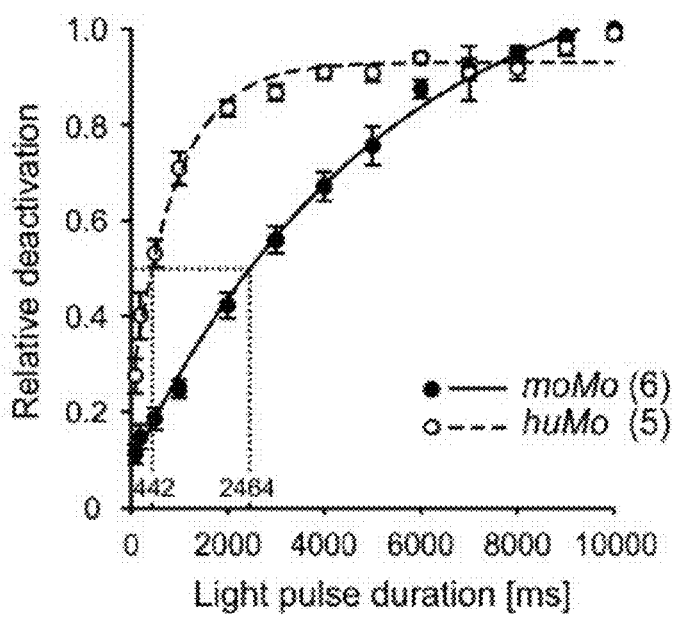
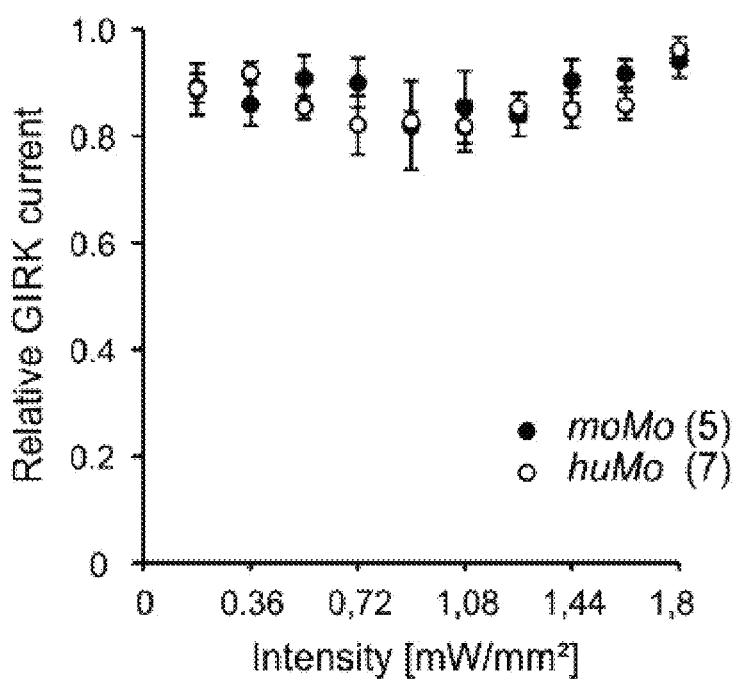
Figs. 11D-E

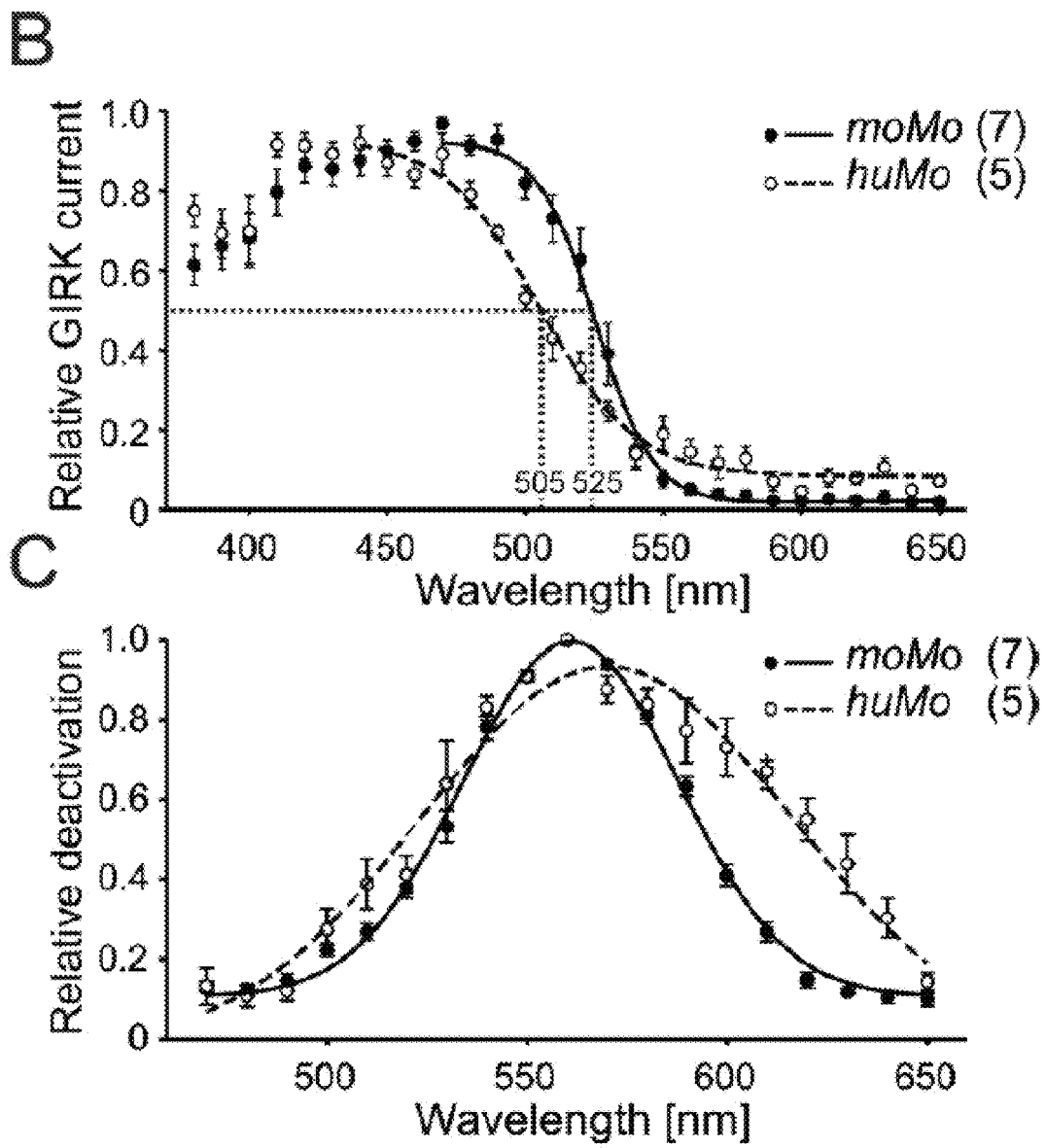
Figs. 12B-C

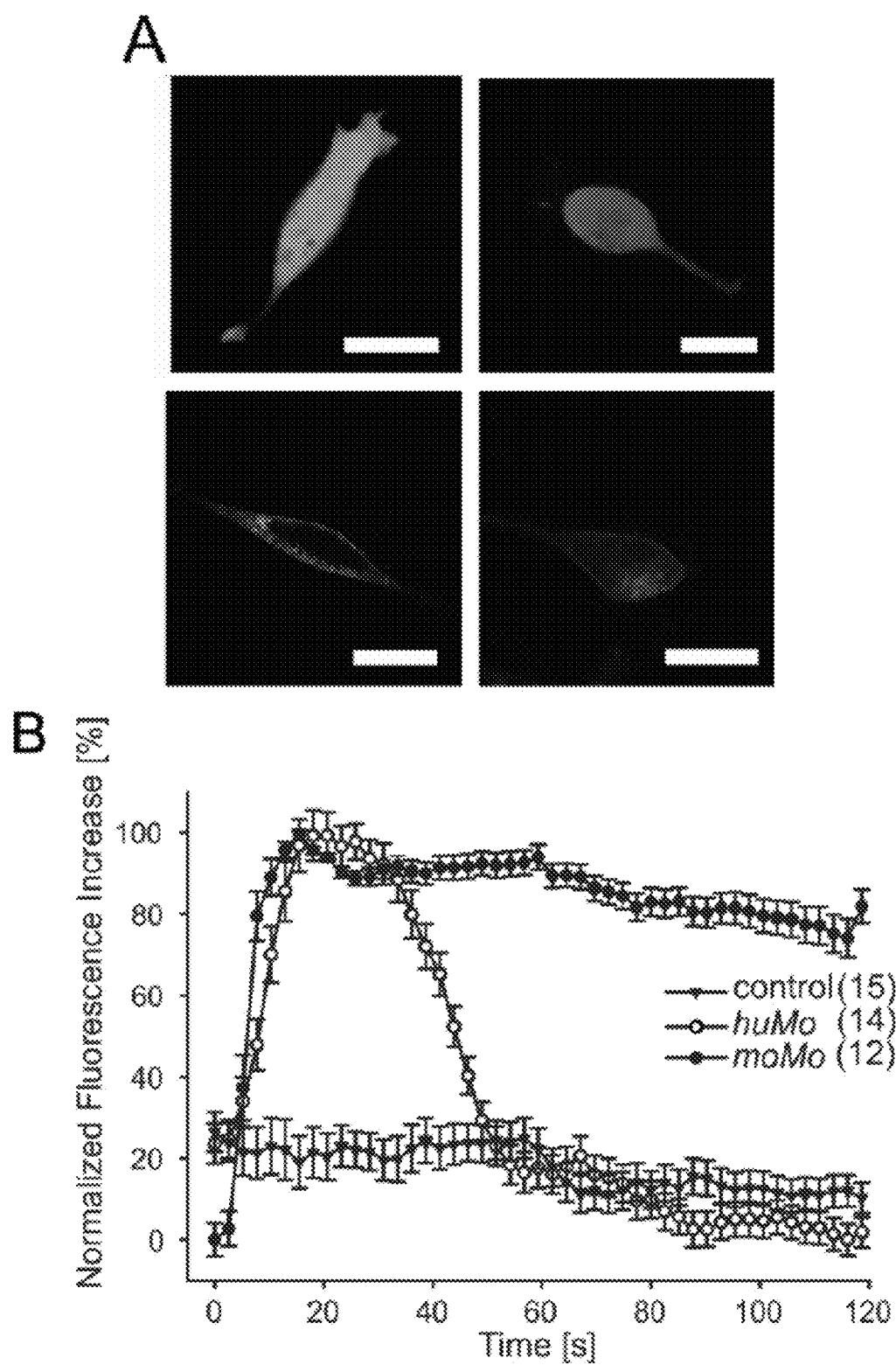
Figs. 13A-B

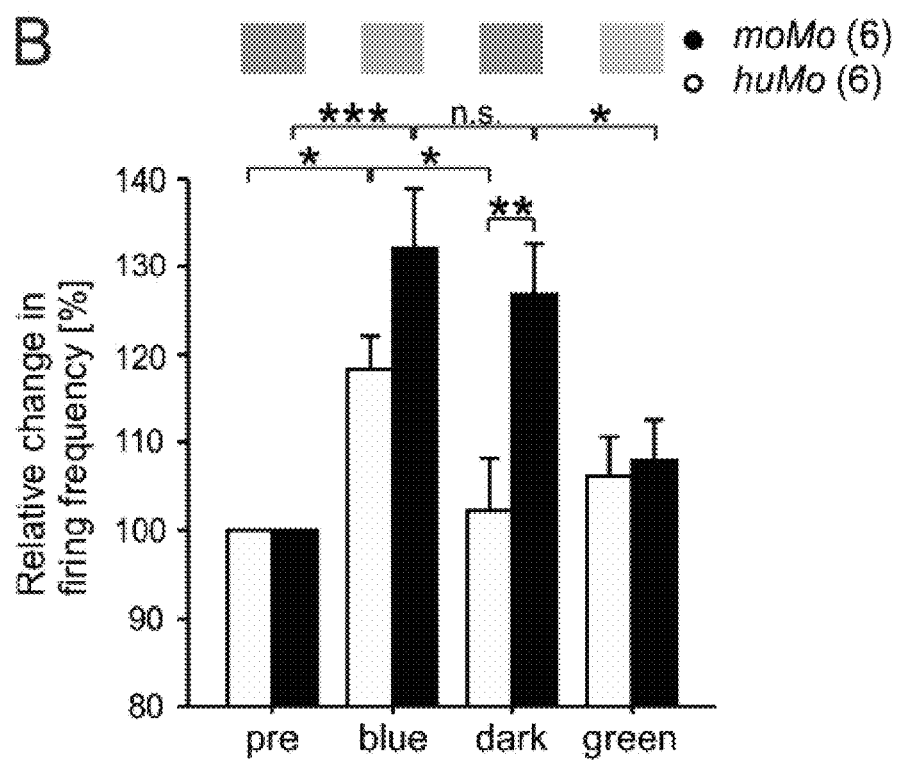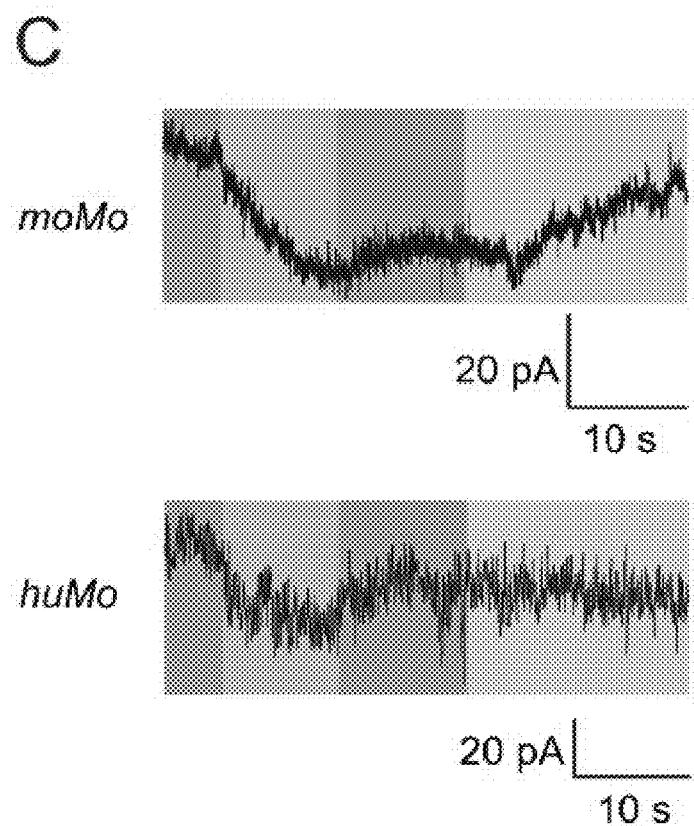
Figs. 14B-C

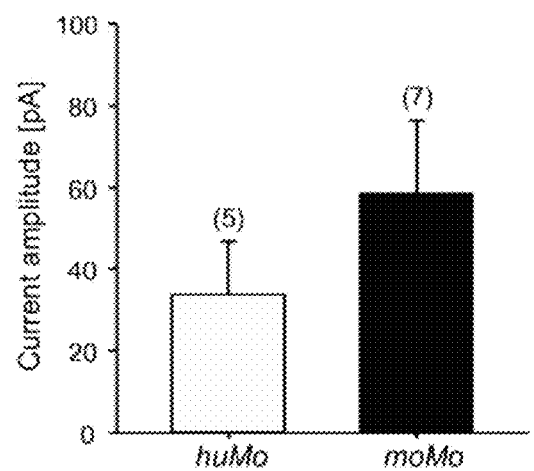
Fig. 14D
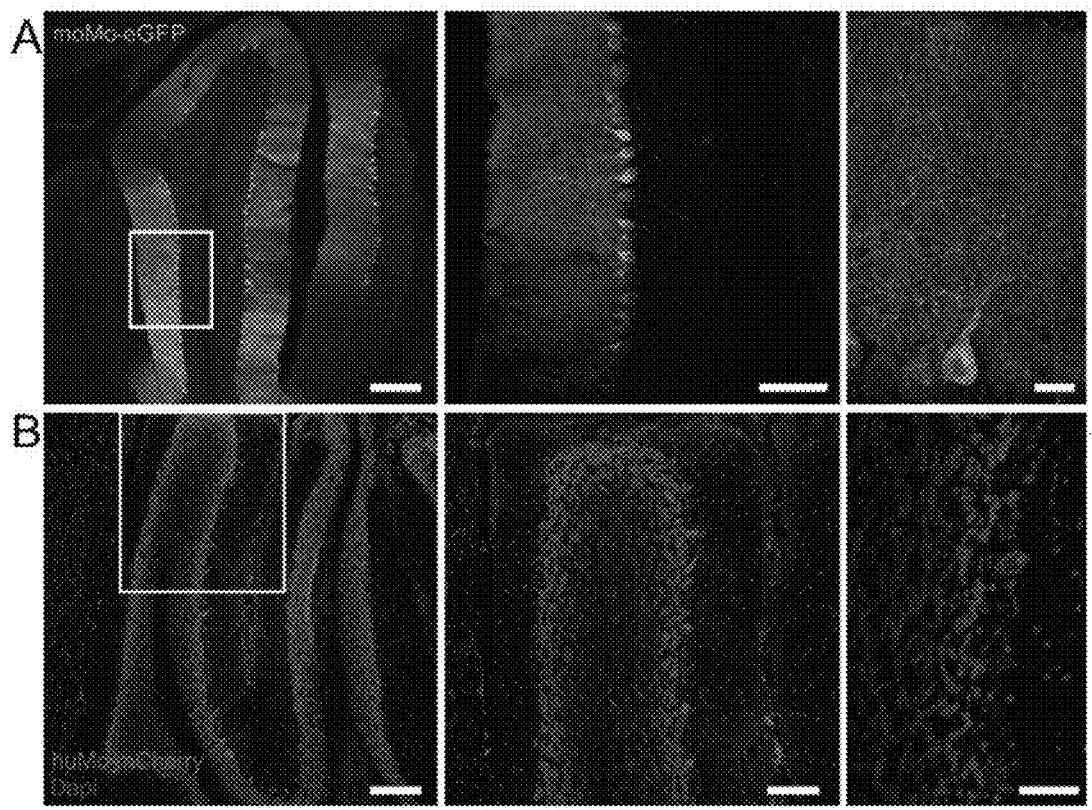
Figs. 15A-B

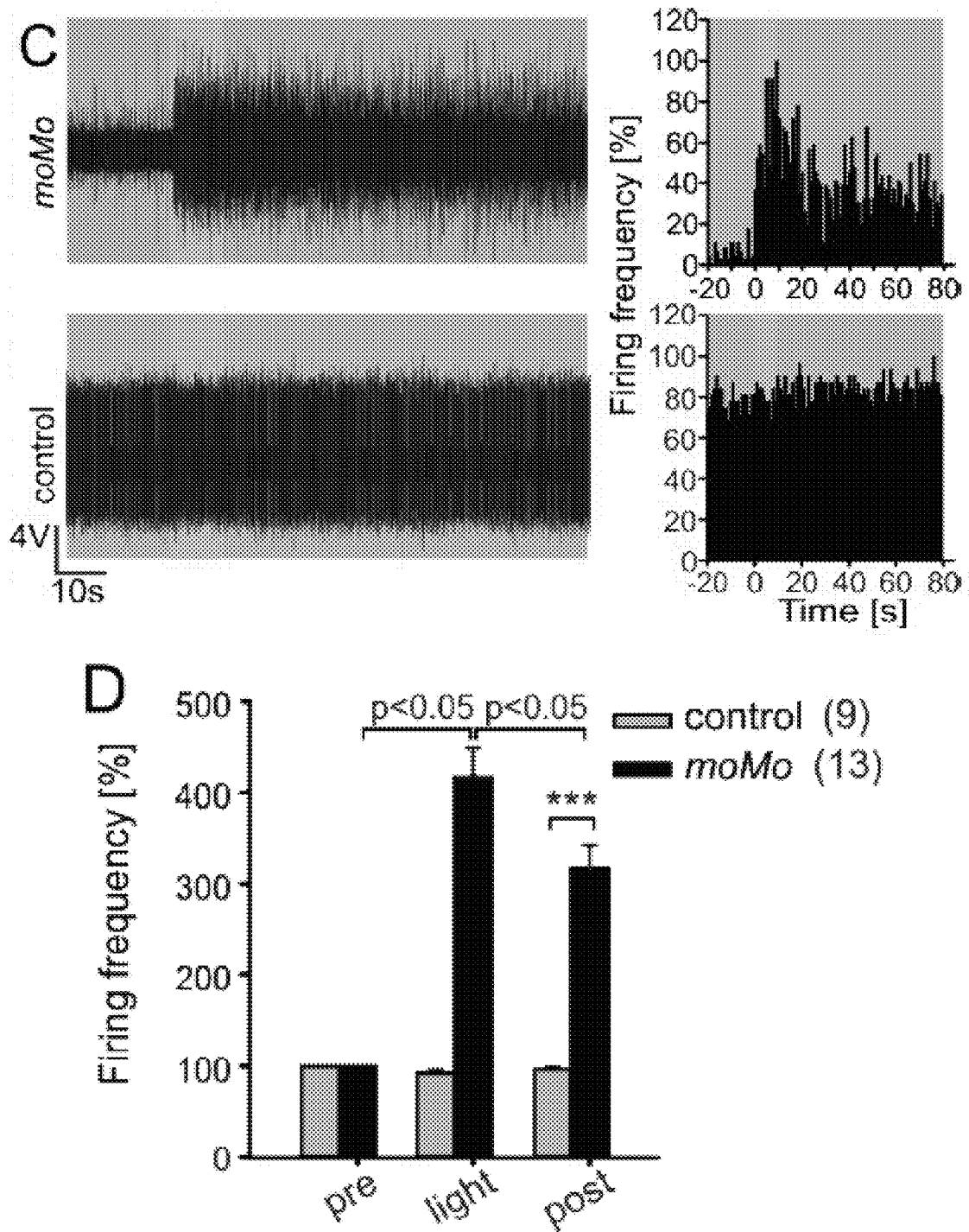
Figs. 15C-D

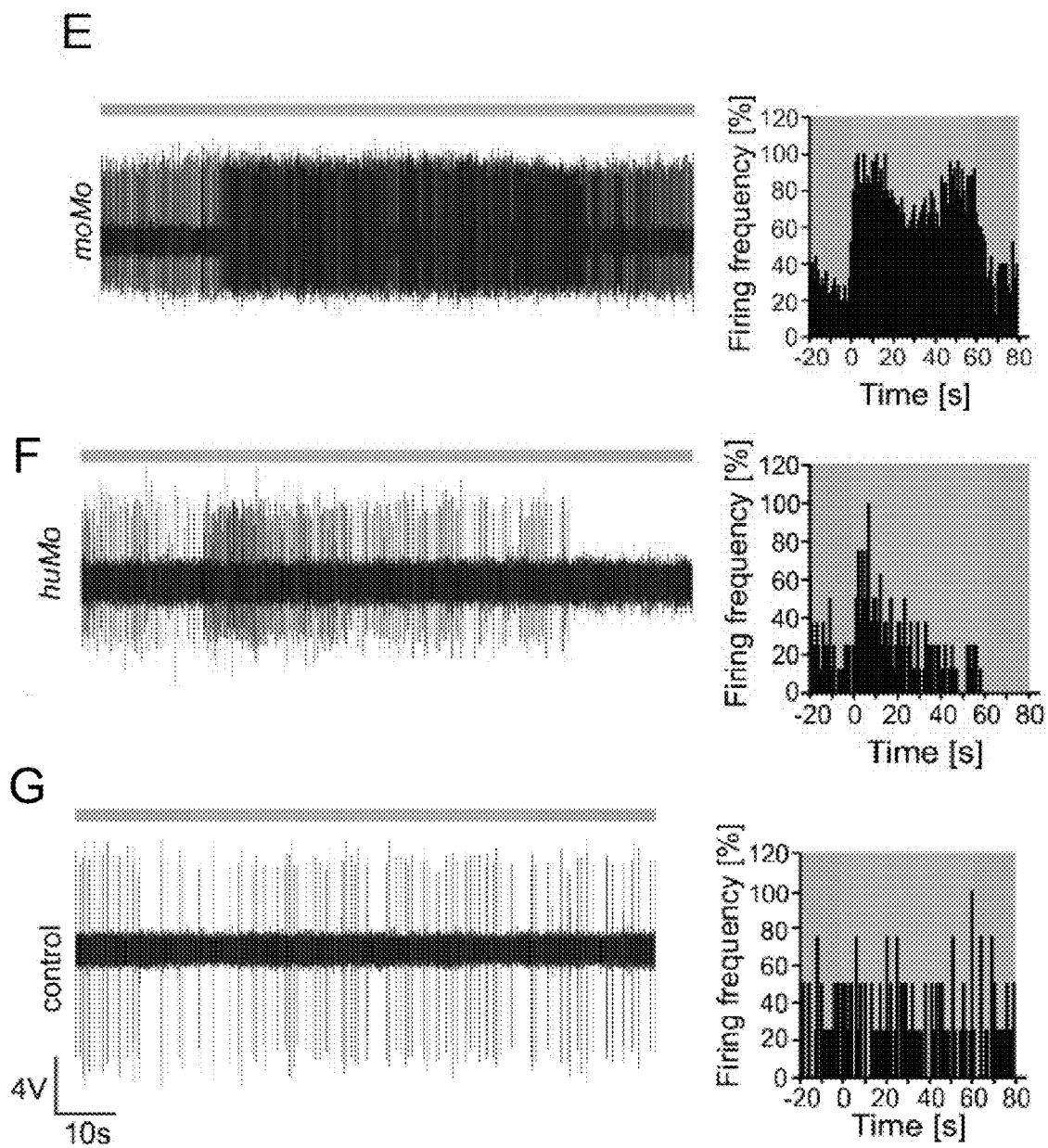
Figs. 15E-G

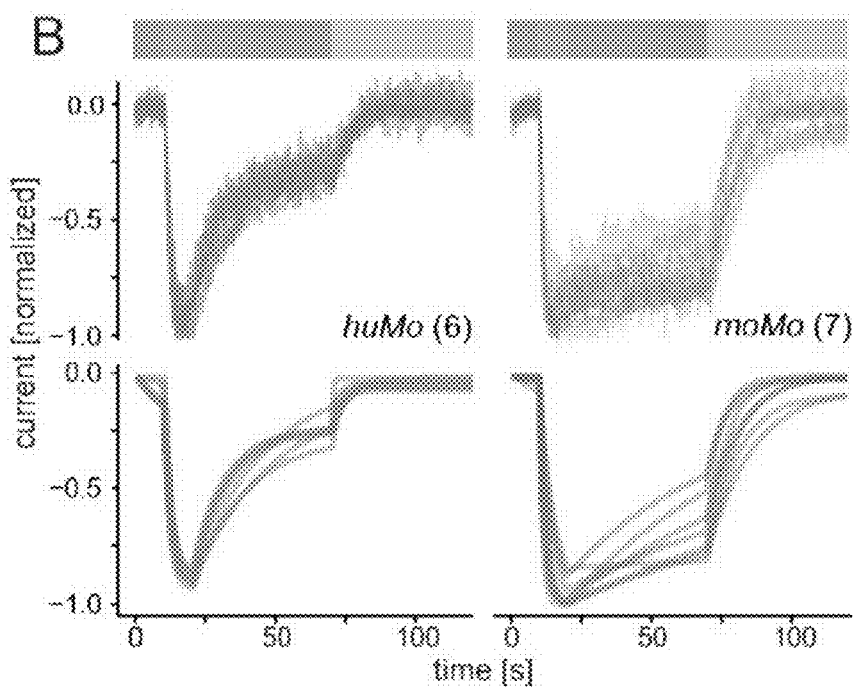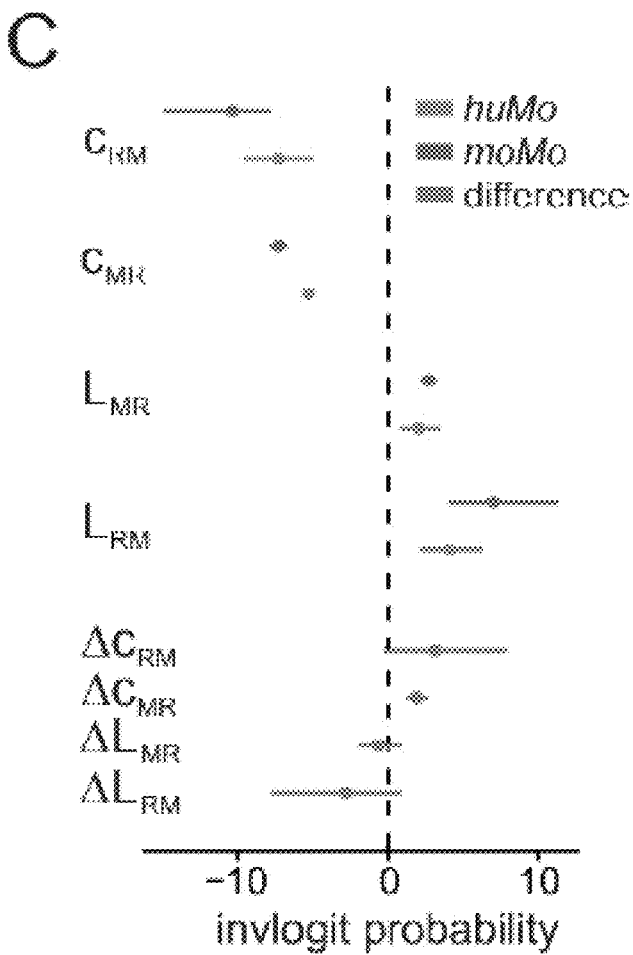
Figs. 16B-C

SYSTEM AND METHOD FOR CONTROLLING G-PROTEIN COUPLED RECEPTOR PATHWAYS

RELATED APPLICATION

This application is a Continuation-in-Part of U.S. patent application Ser. No. 12/375,114, filed Jan. 26, 2009, which is a National Phase Filing of PCT/US2007/074439, filed Jun. 26, 2007, which claims priority from U.S. Provisional Application No. 60/833,378, filed Jul. 26, 2006, the subject matter of which are incorporated herein by reference in their entirety.

GOVERNMENT FUNDING

This invention was made with government support under Grant No. NS047752 awarded by the National Institute of Health. The government has certain rights in the invention.

FIELD OF THE INVENTION

The present invention relates to a light-sensitive G-protein coupled receptor and to a method of controlling G-protein coupled receptor pathways.

BACKGROUND

G-protein coupled receptors (GPCRs) constitute a major class of proteins responsible for transducing a signal within a cell. GPCRs have three structural domains: an amino terminal extracellular domain, a seven transmembrane domain containing seven transmembrane domains, three extracellular loops, and three intracellular loops, and a carboxy terminal intracellular domain. Upon binding of a ligand to an extracellular portion of a GPCR, a signal is transduced within the cell that results in a change in a biological or physiological property of the cell. GPCRs, along with G-proteins and effectors (intracellular enzymes and channels modulated by G-proteins), are the components of a modular signaling system that connects the state of intracellular second messengers to extracellular inputs.

The GPCR protein superfamily can be divided into five families: Family I, receptors typified by rhodopsin and the β-2-adrenergic receptor and currently represented by over 200 unique members (Dohlman et al., Annu. Rev. Biochem. 60:653-688 (1991)); Family II, the parathyroid hormone/calcitonin/secretin receptor family (Juppner et al., Science 254:1024-1026 (1991); Lin et al., Science 254:1022-1024 (1991)); Family III, the metabotropic glutamate receptor family (Nakanishi, Science 258 597:603 (1992)); Family IV, the cAMP receptor family, important in the chemotaxis and development of *D. discoideum* (Klein et al., Science 241: 1467-1472 (1988)); and Family V, the fungal mating pheromone receptors such as STE2 (Kurjan, Annu. Rev. Biochem. 61:1097-1129 (1992)).

G proteins represent a family of heterotrimeric proteins composed of α, β, and γ subunits, that bind guanine nucleotides. These proteins are usually linked to cell surface receptors, e.g., receptors containing seven transmembrane domains. Following ligand binding to the GPCR, a conformational change is transmitted to the G protein, which causes the α-subunit to exchange a bound GDP molecule for a GTP molecule and to dissociate from the β, γ-subunits. The GTP-bound form of the α-subunit typically functions as an effector-modulating moiety, leading to the production of second messengers, such as cAMP (e.g., by activation of adenyl cyclase), diacylglycerol or inositol phosphates. Greater than 20 different types of a-subunits are known in humans. These subunits associate with a smaller pool of β and γ subunits. Examples of mammalian G proteins include Gi, Go, Gq, Gs and Gt. G proteins are described extensively in Lodish et al., Molecular Cell Biology, (Scientific American Books Inc., New York, N.Y., 1995), the contents of which are incorporated herein by reference. GPCRs, G proteins and G protein-linked effector and second messenger systems have been reviewed in The G-Protein Linked Receptor Fact Book, Watson et al., eds., Academic Press (1994).

SUMMARY

Embodiments described herein relate to a light-sensitive G-protein coupled receptor that comprises a light sensitive extracellular domain and a heterologous intracellular domain capable of modulating an intracellular signaling pathway. The G-protein coupled receptor can comprise an opsin with a heterologous intracellular domain. The opsin can be selected from the group consisting of rhodopsins, channelrhodopsins, cone opsins (also known as photopsins), melanopsin (also known as opsin 4 or Opn4, described further below) and various subtypes thereof. In one aspect, the intracellular domain can be coupled to a G-protein subunit to affect at least one G-protein pathway selected from the group consisting of a Gi pathway, a Gq pathway, and a Gs pathway.

In another aspect, the intracellular domain can correspond to at least a portion of the 5HT receptor domain effective to modulate serotonergic signaling. The intracellular domain can comprise an amino acid sequence corresponding to an amino acid sequence of at least one 5HT intracellular loop selected from the group consisting of a 5HT-2A loop, a 5HT-1A loop, and a 5HT-4A loop.

Other embodiments described herein relate to a mammalian cell that includes a light-sensitive G-protein coupled receptor (GPCR), the GPCR being activated by light having a first wavelength and once activated affecting a cell signaling pathway. The GPCR is deactivated by light having a second wavelength and once deactivated inhibits the signaling pathway. The second wavelength is different than the first. In some aspects, the mammalian cell is a nerve cell. In some aspects, the mammalian cell is a brain nerve cell.

In some embodiments, the cell includes a G-protein coupled receptor, which can comprise a light sensitive extracellular domain and a heterologous intracellular domain capable of modulating an intracellular signaling pathway. The light-sensitive G-protein coupled receptor can comprise an opsin with a heterologous intracellular domain. The opsin can be selected from the group consisting of rhodopsins, channelrhodopsins, cone opsins (also known as photopsins), melanopsin (also known as opsin 4 or Opn4, described further below) and various subtypes thereof. The intracellular domain can couple a G-protein subunit to affect at least one G-protein pathway selected from the group consisting of a Gi pathway, a Gq pathway, and a Gs pathway. The intracellular domain can correspond to at least a portion of the 5HT receptor domain effective to modulate serotonergic signaling.

BRIEF DESCRIPTION OF THE DRAWINGS

FIGS. 9(A-C) illustrate wavelength dependent activation and deactivation of GIRK currents in HEK 293 cells by human and mouse melanopsin. (A) Comparison of GIRK channel current traces activated and, following a 50 s dark phase, subsequently deactivated by moMo (top) and huMo (bottom) using 9-cis Retinal (left) or all-trans Retinal (right) and 10/40 s light pulses of 470/560 nm. (B) Comparison of the GIRK current amplitudes activated by huMo and 9-cis retinal (black), huMo and all-trans retinal (medium gray), moMo and 9-cis retinal (dark gray) or moMo and all-trans retinal (light gray) using 10/40 s light-pulses of 470/560 nm. (C) Comparison of activation time constants for GIRK current activation (left) and deactivation time constants for GIRK current deactivation (right) by huMo and 9-cis retinal (black), huMo and all-trans retinal (medium gray), moMo and 9-cis retinal (dark gray) or moMo and all-trans retinal (light gray) using 10/40 s light-pulses of 470/560 nm. Blue boxes: light stimulation using 470 nm light; gray boxes: dark phase without light stimulation; green boxes: light stimulation using 560 nm light; numbers in parenthesis indicate the number of experiments; activation and deactivation constants ($\tau$) were determined by a single exponential fit; values are given as mean ±SEM; *$p<0.05$ ANOVA on ranks with Dunn's Method post hoc analysis.

FIGS. 10(A-E) illustrate desensitization, long-term activation and repetitive activation/deactivation of GIRK currents induced by human and mouse melanopsin. (A) Comparison of light-induced GIRK currents activated and subsequently deactivated by moMo and huMo using 10/40 s light-pulses of 470/560 nm (left). Comparison of long-term, light-induced GIRK currents activated and, following a prolonged dark phase of 300-360 s, subsequently deactivated by moMo and huMo using 10/40 s light-pulses of 470/560 nm (right). (B) Comparison of relative desensitisation (decline of GIRK current amplitude) during dark phase after light stimulation of moMo (black) and huMo (white). (C) Comparison of desensitization time constants for GIRK current activation by moMo (black) and huMo (white) using 10/40 s light-pulses of 470/560 nm. (D) Comparison of GIRK channel current traces activated and subsequently deactivated by moMo and huMo using 1/30 s light pulses of 470/560 nm. (E) Comparison of the maximal GIRK current response during repetitive light stimulation by moMo (black) and huMo (white).

DETAILED DESCRIPTION

Figure 1:
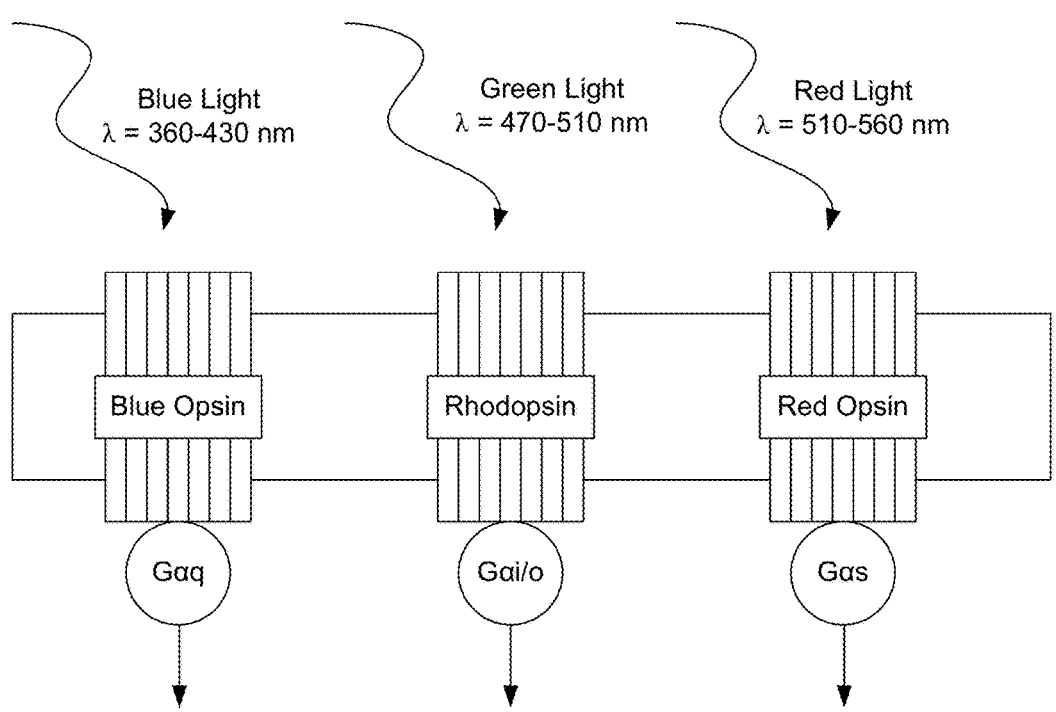
FIG. 1 illustrates the principle of activation of the major GPCR pathways, Gq, Gi/o and Gs by the vertebrate blue opsin (activated by blue light), rhodopsin (activated by green light) and red opsin (activated by red light). GPCR coupling to different G protein pathways is determined by the intracellular protein domains of the GPCR, which will be mutated to allow sufficient coupling of the effector protein.

The present invention relates to light-sensitive (or light-activated) G-protein coupled receptors and to systems and methods of using such GPCRs for controlling GPCR pathways. The light-sensitive GPCRs include a light sensitive extracellular domain and a hetorologous intracellular domain capable of modulating an intracellular signaling pathway.

Embodiments described herein can allow for simultaneous and/or separated activation of any chosen GPCR pathway and can be applied in any type of cell system. The present invention is based on the idea that the extracellular and transmembrane domains of the vertebrate rhodopsin use light energy to activate G-proteins at the intracellular site of a cell. The intracellular G-protein can be transmitted by the intracellular loops of the GPCR of choice (e.g., 5HT receptor subtypes) and introduced into a light-sensitive GPCR (e.g., rhodopsin/opsin) that can be activated by different wavelengths. The intracellular regions of a GPCR determine the G protein specificity, the precise targeting of the GPCR to subcellular structures, such as dendrites and the interaction with intracellular proteins necessary for subtype and cell type specific function.

Embodiments described herein can be combined with a bioluminescence system, such a luciferase system. Co-expression of luciferase and a GPCR in accordance with the present invention, such as blue-green-red light sensitive GPCRs, in a cell allow for internal activation of GPCR pathways. This is important for performing experiments in living animals (e.g., humans) since the system can be activated by intake or infusion of luciferin in a temporal manner. This system and method can also be used to exploit or determine the role of specific GPCR and in particular the cross-talk of GPCRs in disease as well as be used for drug screens. It will be appreciated that the bioluminescence system need not be limited to a luciferase-luciferin system and that other bioluminescence systems can be used in the invention.

It was found that vetebrate (rat) rhodopsin RO4 can be activated by green light and couples to the Gi/o (pertussin toxin sensitive) pathway in heterologous expression systems as well as neurons and neuronal circuits in chicken embryos. Vertebrate rhodoposin can be activated by light without any addition of ligands, such as all-trans retinal in chicken embryos. Moreover, it was found that light application was sufficient to activate rhodopsin in intact embryos and that light could be applied for several hours indicating that light will penetrate the tissue and will not damage the cells.

Additionally, it was demonstrated that luciferase can activate vertebrate rhodopsin and channel rhodopsin 2 when co-expressed in HEK293 cells. Therefore, the system and methods described herein can be used to activate GPCRs or light activated ion channels, such as the green algae channel rhodospin or light activated enzymes controlling second messenger pathways, in vivo, by injection or intake of the luciferase ligand luciferin, which crosses the blood brain barrier.

Accordingly, embodiments described herein relate, in part, to a system for controlling or modulating GPCR pathways. The system can use light to control, for example, the GPCR pathways, Gq (5HT-2A), Gi/o (5HT-1A) and Gs (5HT-4A) within one cell and/or different splice variants within one GPCR family (e.g., 5HT1A,1B,1D) in neuronal circuits and animals. The system includes rhodospins and opsins that are activated by different wavelengths. The intracellular regions of the rhodopsins and the opsins are mutated to allow coupling to the Gi/o, Gs, and Gq pathways.

Activation of the respective pathways can be controlled separately or in concert depending on the wavelength applied. Based on the excitation range of opsin/rhodopsins the different receptors can be controlled simultaneously.

Opsins for use in a light-sensitive GPCR of the present invention can be classified in any of several ways, including function (vision, phototaxis, photoperiodism, etc.), type of chromophore (retinal, flavine, bilin), molecular structure (tertiary, quaternary), signal output (phosphorylation, reduction, oxidation), etc. Opsins for use in a light-sensitive GPCR of the present invention can include but are not limited to rhodopsins, channelrhodopsins, cone opsins (also known as photopsins), melanopsin (also known as opsin 4 or Opn4, described further below) and various subtypes thereof.

Opsins for use in a light-sensitive GPCR of the present invention can include vertebrate opsins. Vertebrate opsins can include but are not limited to bovine, mouse and human vertebrate opsins. In certain embodiments, a light-sensitive GPCR of the present invention can include a cone opsin, such as a vertebrate cone opsin. Vertebrates typically have four cone opsins, long-wave sensitive (LWS, also known as "red opsin" or "L opsin"), short-wave sensitive 1 (SWS1, also known as "blue opsin" or "S opsin"), short-wave sensitive 2 (SWS2), and rhodopsin-like 2 (Rh2) as well as the rod opsin, rhodopsin (Rh1). Additional cone opsins for use in a light-sensitive GPCR of the present invention can include Middle Wavelength Sensitive Opsins 1 (MWS1) and 2 (MWS2), also known as "green opsins".

In some embodiments, intracellular loops derived from GPCRs involved in serotonergic signaling can be selected to study the effects of light activated intracellular signaling pathways mediated by neurotransmitter serotonin. Malfunctions in the serotonergic transmitter system can cause, for example, schizophrenia, depression, anxiety and obesity and drugs acting via serotonergic GPCRs are used to treat patients for their symptoms.

FIG. 1 illustrates one example of a system described herein. The system includes three light-sensitive GPCRs, i.e., blue opsin, rhodopsin, and red opsin, that comprise heterologous intracellular loops. In the system, the intracellular loops of blue opsin are exchanged with 5HT-2A loops for Gq coupling, the intracellular loops of rhodopsin are exchanged with 5HT-1A loops for Gi/o coupling, and the intracellular loops of red opsin are exchanged with 5HT-4A loops for Gs coupling. The system essentially acts a light activated red/green/blue intracellular switch.

G protein specificity of the chimeric light-sensitive GPCRs can be demonstrated in HEK293 cells. Specifically, Gq coupling of the blue opsin/5HT-2A receptor can be demonstrated by monitoring the $Ca^{2+}$ release via activation of phospolipase C/IP3 pathway. Gi/o coupling of the rhodopsin/5HT-1A receptor can be demonstrated by measuring the activation of coexpressed G-protein inward rectifying $K^+$ channels. Gs coupling of the opsin/5HT-4A can be demonstrated by measuring the activation of coexpressed L-type $Ca^{2+}$ channels and AKAP proteins.

In another aspect, Blue-Green-Red switches (e.g., chimeric blue opsin/5HT-2A, rhodopsin/5HT-1A, red opsin/5HT-4A) can be expressed together with luciferase in the serotonergic transmitter system of transgenic mice using the promotor PET-1. PET-1 allows specific expression of the receptors in serotonergic neurons and the activation of the receptors with luciferin. Expression of these chimeric light-activated (or light sensitive) GPCRs within the brain allows for non-invasive control of neurotransmitter signaling with animals and provides a method to readily determine intracellular phenomenons related to mood changes.

It has also been discovered that melanopsin, which is expressed in specific types of retinal ganglion cells, can be used to control at least one G-protein pathway (e.g., Gs, Gi/o and Gq pathways). In addition, it has been shown that a light-sensitive GPCR including an extracellular light-sensitive melanopsin domain can be switched on and off by two different wavelengths of visible light making these GPCRs particular suited for highly-repetitive in vivo applications with high temporal precision and limited phototoxicity. Melanopsins function as a bistable (or tristable) opsin, which means that regeneration of the chromophore occurs in the photoreceptor itself. In the resting state melanopsin contains 11-cis retinal, which is converted to all-trans retinal in the excited state (metamelanopsin) during sustain irradiation.

Therefore, another embodiment relates to a light-sensitive GPCR that includes an extracellular melanopsin domain and a hetorologous intracellular domain capable of modulating an intracellular signaling pathway. Melanopsin variants for use in a GPCR described herein can include a vertebrate melanopsin (vMo) such as a mouse melanopsin (moMo) or human melanopsin (huMo) isoforms. Melanopsin species variants differ in their biophysical properties, such as wavelength dependent activation, activation and deactivation kinetics and receptor desensitization. GPCR signals can be fast (ms to s) and transient, sustained and long-lasting (min to h) or even constitutive. vMo variants can be sufficiently activated by light pulses between about 400 nm to about 480 nm and deactivated by light pulses between about 540 nm to about 580 nm.

Accordingly, the particular melanopsin variant included in a heterologous light-sensitive GPCR described herein can be selected based on the intended use of the GPCR. In some embodiments, a moMo variant opsin can be employed in applications requiring the induction of sustained G-protein pathway activation whereas a huMo variant may employed for applications requiring transient activation.

In certain embodiments, a GPCR including an extracellular melanopsin domain can be switched on by a pulse of blue light and switched off by yellow light. In an exemplary embodiment, a light-sensitive GPCR including an extracellular moMo domain can be switched on by very short pulses of blue light (about 485 nm) and switched off upon exposure to yellow light (about 560 nm). As shown in FIG. 15 and described in the Example below, 100 ms blue light pulses are sufficient to induce sustained (e.g., constitutively active) G protein activation in heterologous expression systems and neurons, which can be used to switch "on" (i.e., activate) cellular GIRK channels, intracellular $Ca^{2+}$ release or cerebellar Purkinhe cells, until yellow light is applied to switch the GPCR receptor to the "off" (i.e., deactivated or nonactive) form.

In particular embodiments, a light-sensitive GPCR including an extracellular melanopsin domain and a hetorologous intracellular domain capable of modulating an intracellular signaling pathway (i.e., a Gi/o or Gq pathway) can be expressed in mammalian cells. In certain embodiments, the mammalian cells include neurons. In an exemplary embodiment, a light-sensitive GPCR including an extracellular melanopsin domain and a hetorologous intracellular domain capable of modulating an intracellular signaling pathway can be expressed in mammalian cells through the use of an adeno-associated viral vector serotype for AAV9.-2YF under the control of a CMV promoter.

The light-sensitive GPCRs can also be expressed, for example, in a heart cell via heart specific promotors for modulating the contractions (or excitability) of the heart, in the spinal cord via HB9 promoter for modulating motor neuron activity after spinal cord injury, and in neural cells or brain areas affected by degenerative diseases, such as Parkinson's disease, to control excitability in the brain area a nerve cells of choice.

EXAMPLE 1

Fast Noninvasive Activation and Inhibition of Neural and Network Activity by Vertebrate Rhodopsin and Green Algae Channel Rhodopsin A major challenge in understanding the relationship between neural activity and development and between neuronal circuit activity and specific behaviors is to be able to control the activity of large populations of neurons or regions of individual nerve cells simultaneously. Recently, it was demonstrated that neuronal circuits can be manipulated by expressing mutated ion channels or G protein-coupled receptors (GPCRs). The application of these techniques to control neuronal function especially in neural circuits and living animals is limited by their relatively slow time course, the complexity of the constructs to be expressed, or the requirement to apply and wash out ligands. To overcome these limitations, we developed molecular probes that could hyperpolarize or depolarize cells on a ms time scale and be used in intact vertebrate systems to examine behavior. To produce hyperpolarization of the somato-dendritic membrane or inhibition of synaptic transmitter release, the GPCR rat rhodopsin 4 (RO4), a member of the vertebrate rhodopsin family, that acts via the Gi/o pathway to regulate excitability by increasing somato-dendritic $K^+$ and decreasing presynaptic $Ca^{2+}$ conductances in neurons, was used. To depolarize the cell membrane, channel rhodopsin (ChR2) from the green algae *Chlamydomonas reinhardtii*, a cation selective channel directly gated by light, was expressed to produce a high $Na^+$ conductance. The properties of these light-activated switches were extensively characterized and shown to be useful for modulating neuronal excitability and synaptic transmission in cultured hippocampal neurons. They were then introduced into the embryonic chick spinal cord and shown to be capable of controlling spontaneous rhythmic activity in isolated cords and living embryos.

Materials and Methods
Plasmid Constructs

For constructing ChR2(1-315)-GFP, cDNA of ChR2 (GenBank accession no. AF461397) was PCR-amplified and cloned into HindIII and SacII sites of pEGFP-N1 (Clontech). SinRep(nsP2S$^{726}$)dSP-EGFP was constructed by subcloning another subgenomic promoter with EGFP into the ApaI site of the original SinRep(nsP2S$^{726}$) following the procedure described in *J. Neurosci. Methods* 133, 81-90, which is herein incorporated by reference. RO4 and ChR2 (1-315) were cloned into the XbaI and MluI sites of SinRep (nsP2S$^{726}$)dSP-EGFP. Muscarinic AChR M2 (human) was cloned into pcDNA3.1(+) and purchased from the UMR cDNA Resource Center (Rolla, Mo.). Sindbis virus vector SinRep(nsP2S$^{726}$) and helper DH-BB were kindly provided by P. Osten (Max Planck Institute for Medical Research, Heidelberg) and RO4 by A. Huber (University of Karlsruhe, Karlsruhe, Germany) (GenBank accession no. Z46957).

Cell Culture

Culturing, maintaining, and transfection of human embryonic kidney (HEK) 293 cells (tsA201 cells) and low-density and autaptic hippocampal neurons were performed. To detect the distribution of RO4 and ChR2, neurons were transfected by using the calcium phosphate method.

Viral Production and Infection

Sindbis pseudovirions were prepared according to Invitrogen's directions (Sindbis Expression System).

Viral titer was ≈1×10$^8$ unit per ml stocked in −80° C. For neuronal infection, viral solution was added to cultured hippocampal neurons on coverslips in 24-well plates. Expression was detected after 10 h and reached maximal expression after 24 h.

Immunocytochemistry and Image Acquisition

Hippocampal neurons (~2-3 weeks in culture) were transfected with RO4 or ChR2-GFP for 24 h, then fixed with 4% paraformaldehyde and permeabilized with 0.2% Triton X-100 in PBS. Anti-opsin (Sigma) and anti-GFP (Molecular Probes) were used to label RO4 and ChR2-GFP. Anti-synaptobrevin-2 (SYSY) was used to colabel neurons with anti-opsin or anti-GFP. Neurons were incubated with primary antibody overnight at 4° C. and after washing they were incubated with Alex 488- and Alex 568-conjugated secondary antibody (Molecular Probes) for 30 min at room temperature. Cells were embedded in Prolong Gold antifade (Molecular Probes). Images were acquired with a Zeiss LSM 410 confocal microscope and analyzed by using VOLOCITY software (Improvision, Lexington, Mass.). Spinal cord whole mounts were stained with the above antibodies as described by Hanson and Landmesser.

Application of Retinal to RO4- or ChR2-Expressing Cells

Bath application of all-trans retinal [100 nM (Sigma)] 2 min before the experiment was sufficient for light activation of both proteins in all preparations tested, i.e., HEK293 cells, cultured hippocampal neurons, and isolated chicken spinal cord. Exogenous application of retinal compounds was not required for light-mediated activation of RO4 and ChR2 in chicken embryos in ovo.

Phototransduction in many systems involves the isomerization of the photosensitive pigment retinal, an aldehyde of vitamin A. Vertebrates and invertebrates use derivatives of 11-cis retinal, whereas bacteria and plants use all-trans isomers as chromophores. Therefore, it was crucial to investigate which retinal compound had to be applied for sufficient activation of the light switches and/or if different tissues or cell types would be able to provide sufficient photosensitive pigments from their own metabolic substrates. We observed that a single bath application lasting 2 min of all-trans retinal or 9-cis retinal [both 100 nM (Sigma)], but not vitamin A, to cultures of HEK293 cells or rat neurons and to isolated embryonic chick spinal cord preparations was sufficient to enable light-driven events during experiments lasting up to 6 h. Whereas retinal was required for light activation of isolated spinal cord preparations after several hours in vitro, freshly isolated cords did not require it. This finding suggested that such compounds might be present in the developing embryo but be washed out during the experiment. Indeed, light was able to elicit movements in embryos in ovo without application of retinal. It is, however, possible that not all tissues will have sufficient amounts of retinal-like compounds to enable light activation without their exogenous application.

Electrophysiology and Data Analysis

For P/Q-type and GIRK channel recordings in HEK293 cells, $Ca^{2+}$ channel ($\alpha_1 2.1$, $\beta_{1\beta}$, and $\alpha_{2\delta}$) or GIRK channel (GIRK1/2) subunits and M2 or RO4 were coexpressed in tsA201 cells, and $Ca^{2+}$ channel-mediated $Ba^{2+}$ or GIRK-mediated K$^+$ currents were measured and analyzed as described (3). For ChR2 recording in HEK293 cells, ChR2 (1-315)-GPF was transfected in tsA201 cells. The pipette solution contained 140 mM KCl, 5 mM EGTA, 2 mM MgCl$_2$, and 10 mM Hepes, pH 7.4, and the bath solution contained 140 mM NaCl, 2 mM MgCl$_2$, 1 mM CaCl$_2$, and 10 mM Hepes, pH 7.4.

Cultured hippocampal neurons were recorded on days 10-14 in vitro 12-24 h after Sindbis virus infection. Extracellular recording solution contained 172 mM NaCl, 2.4 mM KCl, 10 mM Hepes, 10 mM glucose, 4 mM CaCl$_2$, and 4 MgCl$_2$ (pH 7.3); internal solution contained 145 mM potassium gluconate, 15 mM Hepes, 1 mM potassium-EGTA, 4 mM Na-ATP, and 0.4 mM Na-GTP (pH 7.3). For presynaptic inhibition and paired-pulse facilitation, only areas containing a single neuron forming excitatory synapses (autapses) were used. The effect of light on firing was tested by silencing synaptic activity with 1 μM 6-cyano-7-nitroquinoxaline-2,3-dione (Sigma) and 10 μM bicuculline (Sigma). Cells were perfused with 100 nM all-trans retinal (Sigma) for 2 min before the experiment and then perfused with external solution (see Discussion for rationale). Carb (10 μM) (Sigma), 5 nM PTX (Sigma), and 50 μM baclofen (Sigma) were used in experiments when indicated.

Illumination of patches was achieved with a TILL Photonics (Planegg, Germany) Polychrome II monochromator containing a 75-W xenon short arc lamp with an output of 250-690 nm and 475 nm was used to excite ChR2 or RO4. The light intensity was 1×10$^{-6}$ W measured by power meter (Coherent, Santa Clara, Calif.), and the light source was controlled by the EPC9. Light and perfusion traces were programmed in PULSE software.

Spinal Cord Preparation and Measurements

In ovo electroporation, imaging of motor axons, recording of spontaneous bursting episodes in isolated spinal cord preparations, and the quantification of unit activity were as described by Hanson and Landmesser. Statistical significance throughout the experiments was tested with ANOVA by using IGOR software. Standard errors are given as mean+/−SEM.

Results

Vertebrate Rhodopsin can be Used to Inhibit Neuronal Excitability and Synaptic Transmission Vertebrate rhodopsin couples to the G protein transducin, the α-subunit of which belongs to the Gi subfamily, thus raising the possibility that mammalian rhodopsins would couple to other Gi/o family members. In neurons, the pertussis toxin (PTX)-sensitive Gi/o pathway activates G protein inward rectifying potassium channels (GIRKs) and inhibits presynaptic voltage-gated Ca$^{2+}$ channels. GIRK channels are predominantly expressed on dendrites where they can hyperpolarize neurons. Presynaptic Ca$^{2+}$ channels control transmitter release and inhibiting them via Gi/o-coupled receptors inhibits Ca$^{2+}$ influx and transmitter release.

To determine whether vertebrate rhodopsin could be used as a light-activated switch to reduce neuronal excitability postsynaptically and transmitter release presynaptically, RO4 was coexpressed with either GIRK channel subunits 1 and 2 or the P/Q-type Ca2$^+$ channel consisting of the $_{\alpha 1}$2.1, β$_{1b}$, and $_{\alpha 2}$δ subunits. The mAChR M2 (mAChR-M2) was also expressed to serve as a positive control for G protein modulation of GIRK and presynaptic Ca$^{2+}$ channels via Gi/o-PTX-sensitive GPCRs, because it modulates both GIRK and P/Q-type Ca2$^+$ channels in vivo and in heterologous expression systems. We first demonstrated in HEK cells that both of these channels were modulated by light activation of RO4 in a manner very similar to their modulation via mAChR-M2.

Figure 6:
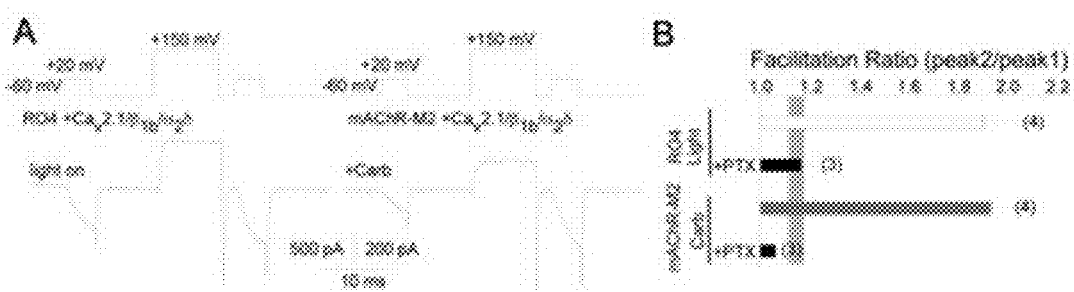
FIGS. 6(A-B) illustrate activation of vertebrate rhodopsin induces paired-pulse facilitation of P/Q-type $Ca^{2+}$ channels is comparable to the mAChR-M2 induced facilitation. (A) $Ba^{2+}$ current traces of P/Q-type $Ca^{2+}$ channels documenting prepulse facilitation induced by the vertebrate rhodopsin RO4 (Left) or mAChR-M2 (Right) activation. From a holding potential of −60mV a 5-ms-long first test pulse to +20mV was elicited. After 1 s a 10- ms-long prepulse to +150 mV was elicited 2 ms before a second 5-ms-long test pulse to +20 mV. The peak current elicited by the second 5-ms test pulse was compared with the peak current elicited by the first 5-ms test pulse and is given as the facilitation ratio (B). (B) Facilitation ratio of P/Q-type $Ca^{2+}$ currents during GPCR activation. Facilitation ratio was determined by dividing the peak current elicited by the second test pulse by the peak current elicited by the first test pulse for the protocol shown in A. In the presence of 50 μM PTX the G protein-mediated inhibition of the $Ca^{2+}$ channel is blocked. Therefore no facilitation is observed.

Activation of the GPCRs by either light or the AChR agonist carbachol (Carb) increased GIRK-mediated K$^+$ currents by comparable amounts (FIGS. 2A and B) and with comparable activation and deactivation kinetics (FIGS. 2C and D). Importantly, light activation of RO4 was blocked by prior application of PTX, indicating that activation of GIRK channels by vertebrate rhodopsin is mediated via PTX-sensitive pathways (FIG. 2B). The amount of desensitization during long light or ligand exposure times was modest and comparable between the two [8.7±0.8% (n=4) for mAChR-M2 and 8.7±1.1% (n=4) for RO4], indicating that RO4 can be activated by light over long time periods. When RO4 and mAChR-M2 were coexpressed with the P/Q-type Ca$^{2+}$ channel, light caused reversible inhibition of the Ca$^{2+}$ currents (FIGS. 2E and G and FIG. 6). Light or Carb caused a similar shift in the voltage dependence of activation to more depolarized potentials (FIG. 2F). In addition, the G protein inhibition caused by light was reversed by high positive prepulses applied shortly before a test pulse (FIG. 6) over a voltage range between −10 and −65 mV (data not shown) similar to the inhibition caused by Carb. Furthermore, light mediated channel inhibition was inhibited by PTX (FIG. 6). The time constants for onset of inhibition and reversal of inhibition were also comparable between RO4 and mAChR-M2 ($\tau_{on}$=3-7 s, $\tau_{off}$≈20-60 s, FIGS. 2G and H). Thus, vertebrate rhodopsin modulates GIRK and P/Q-type Ca$^{2+}$ channels via PTX-sensitive pathways with similar efficacy and activation and deactivation kinetics as the mAChR.

Figure 2:
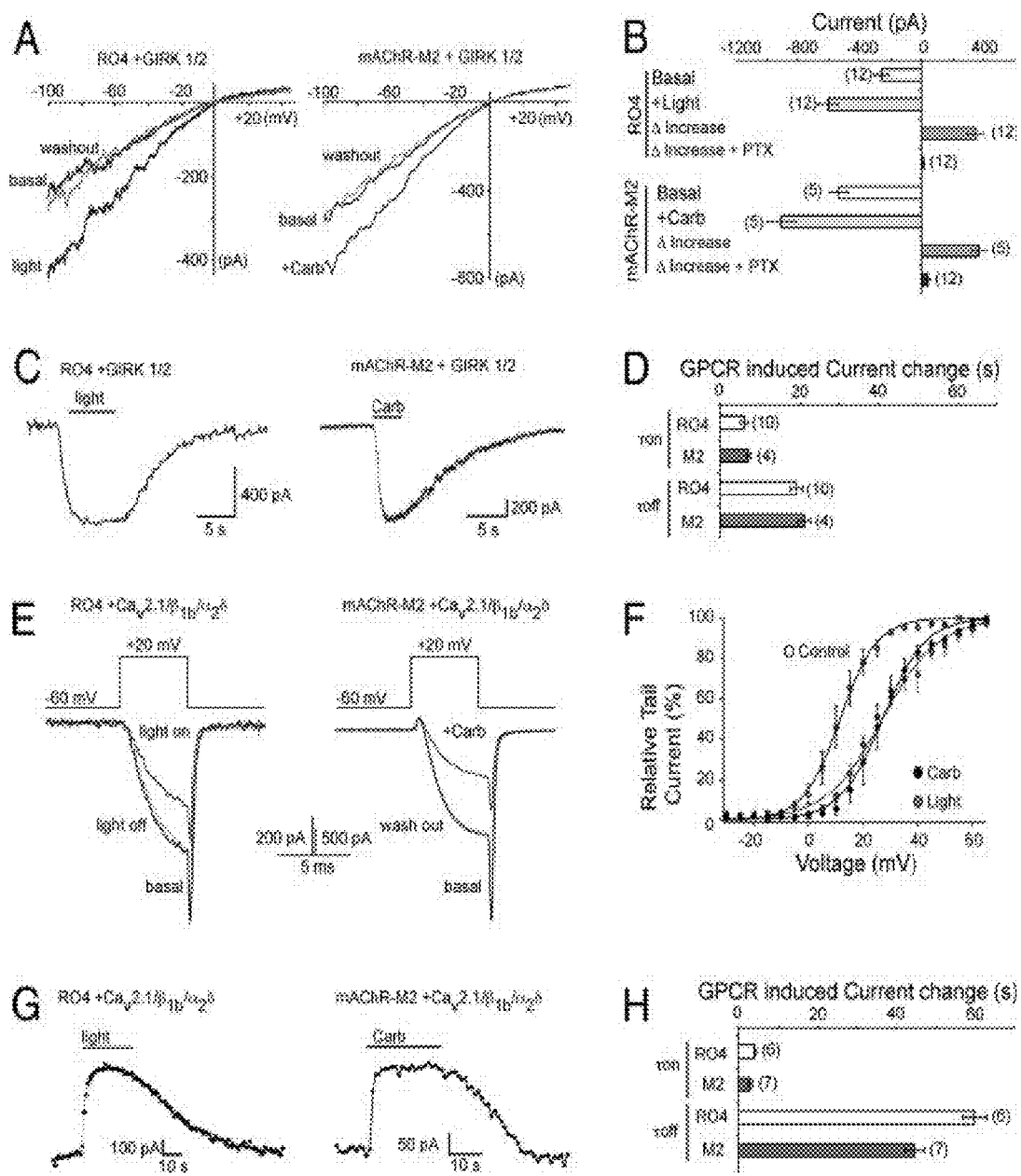
FIGS. 2(A-H) illustrate plots showing vertebrate rhodopsin modulates GIRK and P/Q-type $Ca^{2+}$ channels via Gi/o-PTX-sensitive pathways. (A) $K^+$ current traces of GIRK1/2 channels coexpressed with RO4 or mAChR-M2 in HEK293 cells before, during, and after light stimulation (Left) or 10 µMCarb application (Right). Currents were elicited by 500-ms voltage ramps from −100 to +50 mV. (B) Comparison of the GPCR-induced current increase in the presence and absence of 5 nmol PTX. (C) Time course traces of GPCR-mediated activation of GIRK currents. GIRK currents were recorded at −60 mV. (D) Comparison of the time constants of the GPCR-induced GIRK current changes before and after GPCR activation. (E) $Ba^{2+}$ current traces of P/Q-type $Ca^{2+}$ channels ($_{\alpha 1}2.1$, $\beta_{1b}$, and $_{\alpha 2}\delta$ subunits) coexpressed with RO4 or mAChR-M2 in HEK293 cells before, during, and after light stimulation (Left) or 10_MCarb application (Right). (F) GPCR induced depolarizing shift in the voltage dependence of activation curve of P/Q-type $Ca^{2+}$ currents. Currents were elicited from a holding potential of −60 mV by 5-ms-long, 5-mV voltage steps from −10 to +65 mV. Relative tail currents were plotted against the voltage pulses. (G) Time course traces of GPCR-mediated inhibition of P/Q-type $Ca^{2+}$ currents. $Ba^{2+}$ currents were elicited by voltage pulses from −60 to +20 mV and measured every s. (H) Comparison of the time constants of the GPCR-induced P/Q-type channel current changes before and after GPCR activation. Throughout all experiments number in parentheses indicate the number of experiments and statistical significance as indicated (*, $P<0.05$; **, $P<0.01$, ANOVA).
Figure 3:
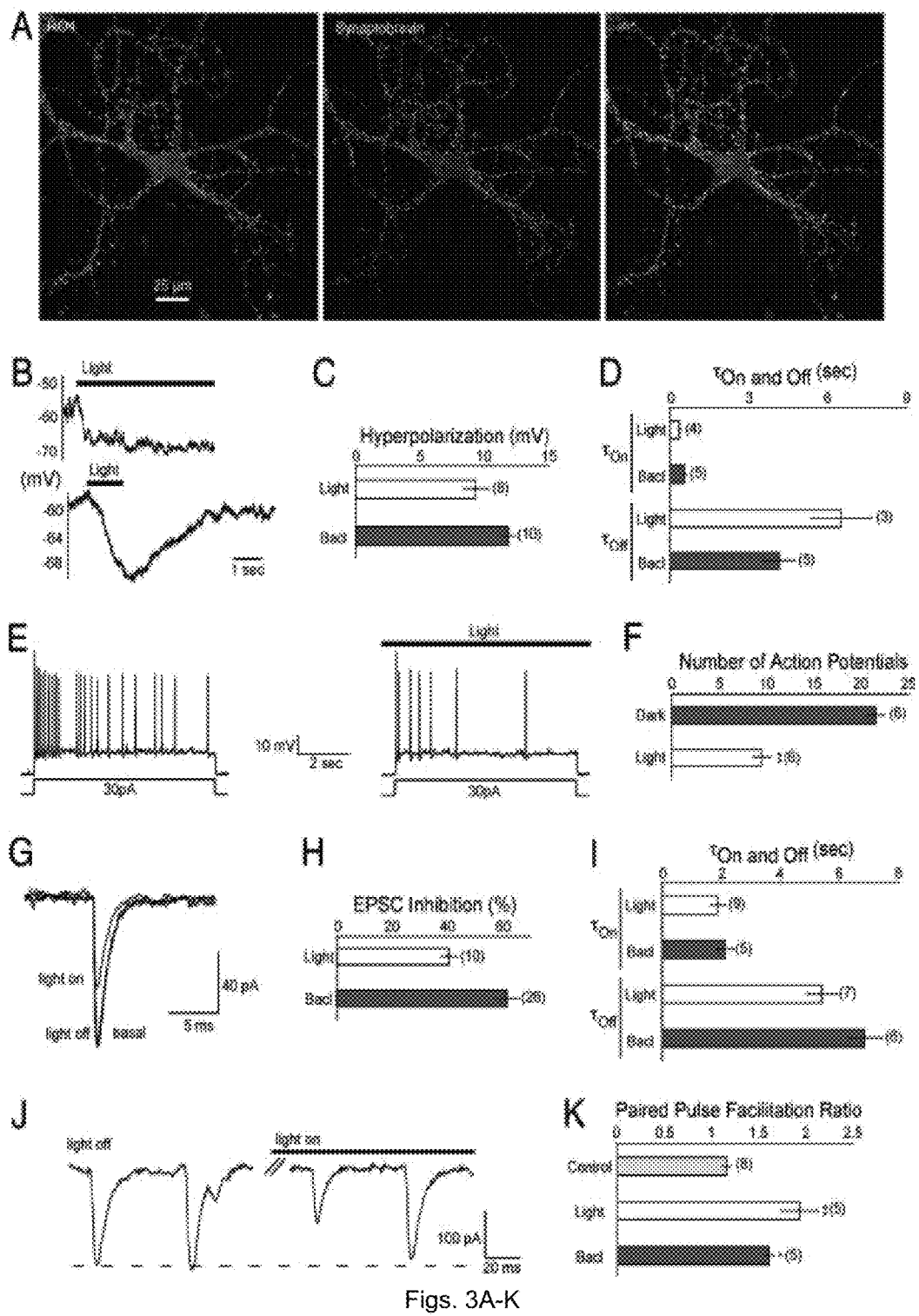
FIGS. 3(A-K) illustrate functional expression and characterization of vertebrate rhodopsin in cultured hippocampal neurons. (A) Colocalization of RO4 and synaptobrevin in cultured hippocampal neurons. (Left) Fluorescence patterns of neurons from low density hippocampal cultures transfected with RO4 reveal a punctate staining. RO4 was detected with an anti-RO4 antibody and visualized with an Alexa 488-coupled secondary antibody. (Center) Hippocampal cells were stained with an antisynaptobrevin II antibody and visualized with an Alexa 568-coupled secondary antibody. (Right) Overlay of RO4 and synaptobrevin II staining. Yellow indicates colocalization. (B) RO4 induced voltage change during a long (Upper) and short (Lower) light pulse. (C) Average GPCR (RO4, GABAB)-induced hyperpolarization of cultured hippocampal neurons. Throughout the experiments GABAB receptors were activated by application of 50 µM baclofen (Bacl). (D) Time course of GPCR (RO4, GABAB)-induced hyperpolarization and recovery from hyperpolarization after switching off the light or washing out baclofen. (E) Voltage traces of current-induced (30 pA) neuronal firing of cultured hippocampal neurons before and during light activation of RO4. (F) Comparison of the number of action potentials measured after current injection for a neuron before and during light activation of RO4. (G) Comparison of EPSC amplitude before, during, and after light application for EPSCs measured in autaptic hippocampal cultures expressing RO4. EPSCs in autaptic hippocampal neurons were elicited by 2-ms voltage pulses from −60 to +10 mV. (H) Comparison of GPCR (RO4, GABAB)-induced EPSC inhibition measured in autaptic hippocampal neurons. (I) Time constants of GPCR (RO4, GABAB)-induced EPSC inhibition and release from inhibition. EPSCs were elicited every 5 s as described in G. (J) Autaptic EPSC traces elicited by 2-ms voltage pulses from −60 to +10 mV separated by 50 ms (20-Hz stimulation) before and after light activation of RO4. (K) Comparison of paired pulse facilitation before and after GPCR (RO4, GABAB) activation for a 20-Hz stimulation protocol. The amplitude of the second EPSC was compared with the first EPSC.

Because RO4 activates GIRKs, which control excitability postsynaptically, and inhibits Ca$^{2+}$ channels of the Ca$_v$2 family, which trigger transmitter release presynaptically, we next investigated in cultured hippocampal neurons whether light activation of RO4 could hyperpolarize neurons somato-dendritically to decrease their firing as well as inhibit presynaptic Ca$^{2+}$ influx to modulate short-term synaptic plasticity such as paired-pulse facilitation. Exogenously expressed RO4 was localized somato-dendritically and transported to 70-80% of the synaptic sites where it colocalized with the presynaptic neuronal marker synaptobrevin II (FIG. 3A). Light activation of RO4 induced a 9-mV hyperpolarization within ms comparable to the hyperpolarization induced by activation of endogenous GABA$_B$ receptors by 50 μM baclofen (FIGS. 3B and C). The hyperpolarization was stable during light application (measured up to 30 s) but was rapidly reversed when the light was switched off (FIGS. 3B and D). The time constants for hyperpolarization and repolarization were much faster than in HEK293 cells (compare FIGS. 3D and 2C) probably because of the effect of endogenous proteins, such as RGS proteins, which accelerate the GTPase activity of the G proteins. These observations are comparable to the described actions of Gi/o-coupled receptors on membrane changes in neurons. More importantly, the hyperpolarization induced by light was capable of reducing the number of action potentials produced during a depolarizing current pulse (FIGS. 3E and F).

Because RO4 appeared to be localized at synapses and inhibits P/Q-type Ca$^{2+}$ channels in HEK293 cells, we investigated whether light activation of RO4 could be used to control presynaptic function. We analyzed facilitation properties before and after light application and compared these to the effect of activating the GABA$_B$ receptor with baclofen (FIG. 3G-K). Light activation of RO4 reduced the excitatory postsynaptic current (EPSC) amplitude by 40% compared with 60% when the GABAB receptor was activated (FIGS. 3G and H), presumably because of a reduction in quantal content. The time constants for these effects were comparable for both receptors [$\tau_{on}$=0.3-0.6 s, $\tau_{off}$≈4-6 s (FIG. 3I)]. As would be expected if this reduction of EPSC amplitude was caused by a reduction in quantal content, paired-pulse facilitation for both receptor types was increased (FIGS. 3J and K). Taken together, these results show that light activation of RO4 can be used to control cell excitability via hyperpolarization of the somatodendritic membrane as well as presynaptically via reduction of transmitter release.

Figure 7:
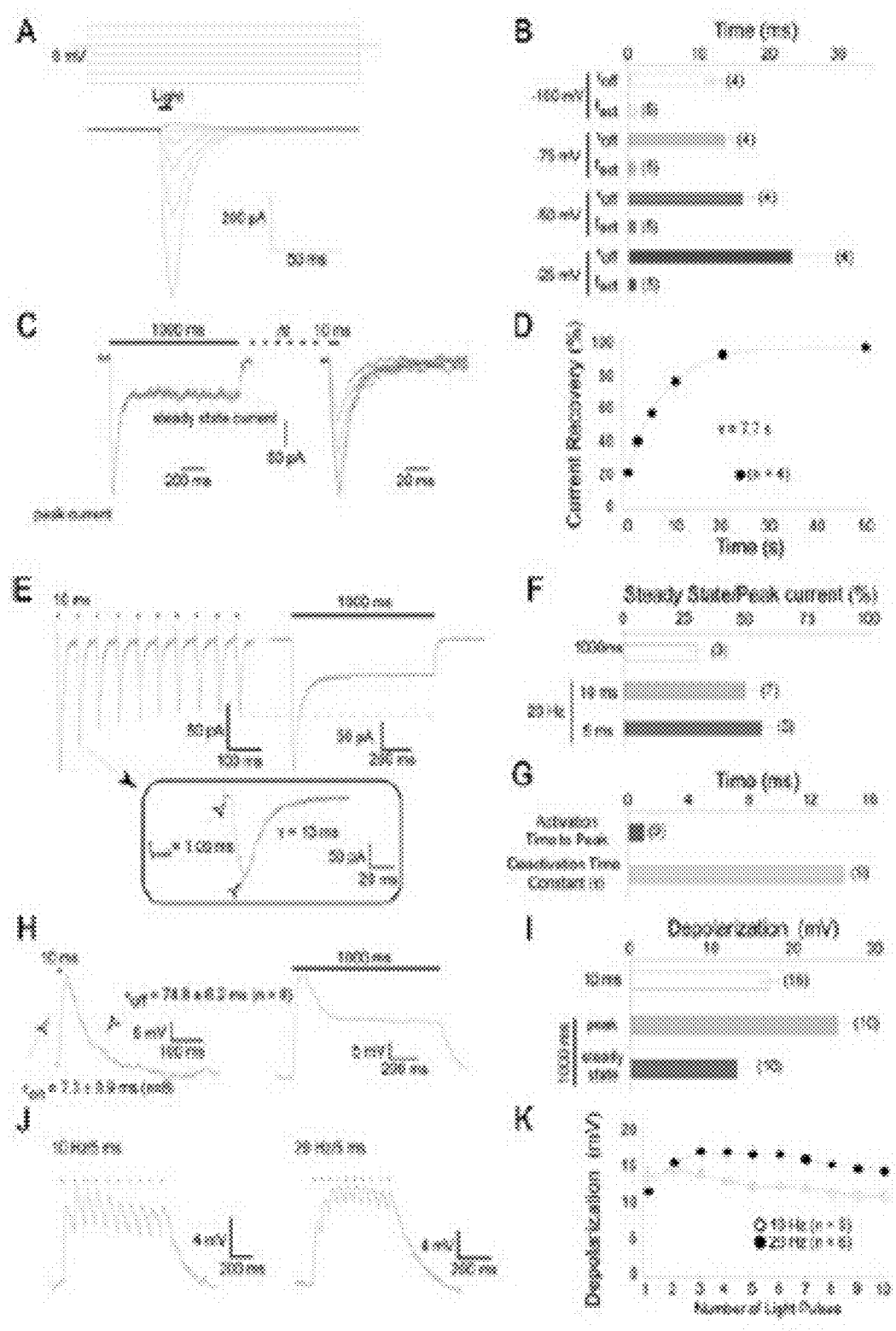
FIGS. 7(A-K) illustrate biophysical characterization of the C terminally truncated, GFP-tagged ChR2 in HEK293 cells. (A) Light-induced ChR2 currents in HEK293 cells after a 10-ms light pulse. Step potentials were from −100 to +50 mV in 25-mV steps. The current traces reveal the inward rectifying behavior of ChR2. (B) Activation and deactivation time constants for ChR2 currents after 10-ms light pulses for the indicated potentials. The deactivation time constant is voltage dependent. The more depolarized the cell the slower is the deactivation of ChR2 currents. (C) Light-induced ChR2 currents measured at −60 mV for the recovery of steady-state current to peak current. (D) Peak current recovery for ChR2 currents after a 1,000-msec light pulse. C and D show that the peak current recovers to 100% of its original value within 20-30 s. (E) Comparison between light-induced ChR2 currents using 10- to 20-Hz/10-ms light pulses in comparison with a continuous 1,000-ms light pulse. (Inset) The second current within the 20-Hz/10-ms light pulse protocol is shown on a larger time scale. The ChR2 activates within a ms. (F) Comparison between light-induced current reduction for ChR2 currents elicited by different light stimulation protocols. E and F illustrate that the shorter the light pulses for ChR2 activation the smaller is the ChR2 current reduction relative to the maximal peak currents. Thus during a prolonged light pulse the ChR2 steady-state current is more reduced than during repetitive, short light stimulation protocols. (G) Activation and deactivation time for ChR2 currents elicited with 10-ms light pulses at −60 mV. (H) Traces of light (ChR2)-induced voltage changes in HEK293 cells after 10-ms (Left) or 1,000-ms (Right) light activation of ChR2. (I) Light-induced depolarization mediated by ChR2 for 10- and 1,000-ms light duration. H and I illustrate the time course of the membrane voltage changes during activation and deactivation of ChR2 and demonstrate that the voltage changes are much slower than the underlying current changes. (J) Traces of light (ChR2)-induced voltage changes during a 10- or 20-Hz protocol with 5-ms light pulses. (K) Light-induced depolarization mediated by ChR2 during light trains with different frequencies. J and K illustrate that during repetitive stimulations with frequencies >5 Hz the voltage change mediated by ChR2 current is additive at high-frequency, short-duration light pulses.

Green Algae ChR2 can be Used to Precisely Drive Neuronal Firing on a Fast (ms) Time Scale ChRs are microbial type rhodopsins with an intrinsic light-gated cation conductance. ChR1 from *C. reinhardii* is specific for protons, whereas ChR2 is a less selective cation channel with conductance for $H^+>>Na^+>K^+>Ca^{2+}$. Because the conductance of ChR2 is higher than that of ChR1 and the C terminally truncated version of ChR2 (1-315) is as active as the full-length protein, all experiments were carried out with the ChR2 (1-315) fragment fused to GFP at the C-terminal end of ChR2 (1-315). To test whether the ChR2 can act to depolarize cells when activated by light, ChR2 (1-315) was first expressed and extensively characterized in HEK293 cells (FIG. 7). Light activation of ChR2 was found to cause depolarizations of 10-25 mV within 10 ms, with repolarization occurring within 200 ms. Thus ChR2 should be capable of depolarizing neurons sufficiently to elicit action potentials.

Figure 4:
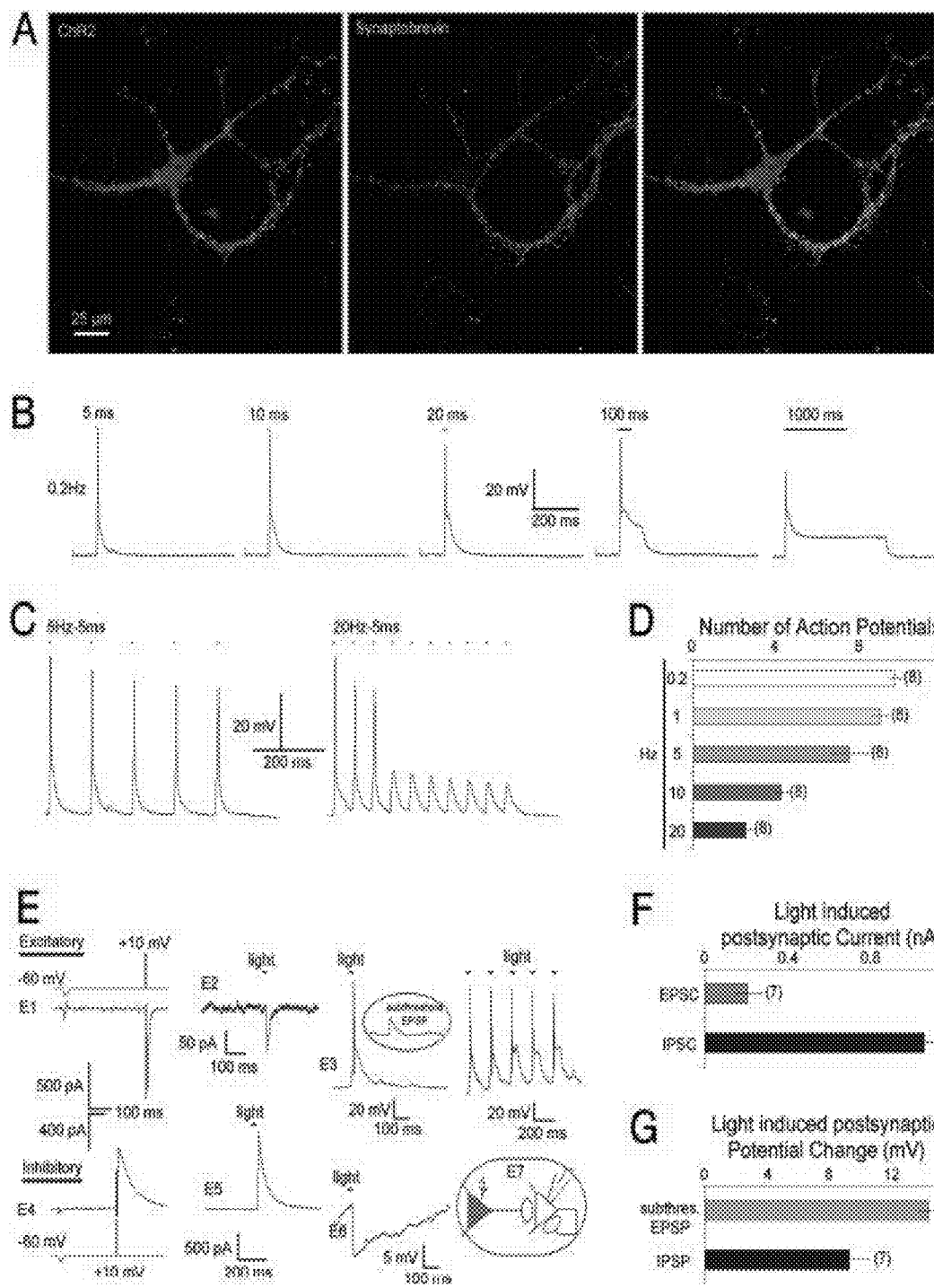
FIGS. 4(A-G) illustrate functional expression and characterization of green algae ChR2 in cultured hippocampal neurons. (A) Colocalization of ChR2 and synaptobrevin in cultured hippocampal neurons. (Left) Fluorescence patterns of neurons from low-density hippocampal cultures transfected with GFP-ChR2 reveal a punctate staining. (Center) Hippocampal cells were stained with an antisynaptobrevin II antibody and visualized with an Alexa 568-coupled secondary antibody. (Right) Overlay of GFP-ChR2 and synaptobrevin II staining. Yellow indicates colocalization. (B) Voltage traces of ChR2-induced neuronal firing of cultured hippocampal neurons for light stimuli with increasing duration. (C) Voltage traces of ChR2-induced neuronal firing of cultured hippocampal neurons for light stimuli with different frequencies. (D) Number of action potentials measured in neurons expressing ChR2. Action potentials were elicited by a train of 10 stimuli for different light stimulation frequencies with a light duration of 5 ms. (E) Light activation of ChR2 expressed in excitatory (Upper) or inhibitory (Lower) presynaptic neurons induce activation or inhibition in the paired postsynaptic neurons. (E1 and E4) EPSC (Upper) or IPSC (Lower) were elicited by a 2-ms voltage pulse from −60 to +10 mV in the postsynaptic autaptic neuron. (E2 and E5) Light activation of the excitatory and inhibitory presynaptic cells expressing ChR2 induced EPSC (Upper) or IPSC (Lower) on the postsynaptic, autaptic neurons. (E3) Presynaptically (excitatory) light induced spiking or subthreshold depolarization (Inset) of the postsynaptic neuron after a single 5-ms light pulse (Left) or a 10-Hz/5-ms light stimulation protocol (Right). Five light pulses were applied. (E6) Presynaptically (inhibitory) light induced hyperpolarization of the postsynaptic neurons after a single 5-ms light pulse. (E7) Schematic diagram of the neuronal circuit analyzed. Gray indicates the presynaptic neuron expressing ChR2. (F) Average amplitude of the light induced EPSCs or IPSCs. (G) Average amplitude of the light induced hyperpolarization (IPSP) or depolarization (EPSP), when the depolarization was not sufficient to trigger an action potential.

When exogenously expressed in hippocampal neurons, ChR2 appeared to localize both somato-dendritically and at 50-70% of the synaptic sites defined by synaptobrevin 2 immunostaining (FIG. 4A). A 5-ms light activation was sufficient to elicit action potentials in >90% of the experiments performed, whereas longer light exposure led to continuous subthreshold depolarization of the neurons (FIG. 4B). When stimulated at 5 Hz most stimuli elicited action potentials, but as the frequency of stimulation was increased, the proportion that triggered subthreshold EPSPs increased (FIGS. 4C and D). We next tested whether presynaptically expressed ChR2 was capable of triggering synaptic transmission on postsynaptic neurons. Pairs of hippocampal neurons were analyzed, in which a GFP-ChR2 expressing neuron synapsed with a ChR2-negative neuron that had formed autapses on its own soma (FIG. 4E, $E_7$ diagram). We found that inhibitory postsynaptic currents (IPSCs) as well as EPSCs could be successfully triggered by light activation of the presynaptic neuron (FIG. 4E). The light-activated currents were different in amplitude than the autaptic currents elicited by electrically stimulating the postsynaptic neuron (FIG. 4E), indicating that they are mediated through different neuronal contacts. In three of seven experiments light-activated postsynaptic EPSCs were sufficient to trigger somato-dendritic firing up to 20 Hz. In the remaining four experiments subthreshold EPSPs were observed (FIG. 4E, $E_3$). Light-induced postsynaptic IPSCs caused somatodendritic hyperpolarization (FIG. 4E, $E_6$). As expected the IPSC/ EPSC amplitudes and degree of hyperpolarization or depolarization varied between analyzed neuronal pairs, as they would depend on the amount of synaptic contacts formed between the presynaptic and postsynaptic neuron (FIGS. 4F and G).

Activation of RO4 and ChR2 can be Used to Control Spontaneous Activity in Isolated Intact Spinal Cords and Living Embryos Our next goal was to show that these light-sensitive proteins could be used to control circuit behavior in whole animal preparations. Early embryonic chick spinal cords exhibit rhythmic episodes of spontaneous bursting activity, which are generated by recurrent excitatory connections between motoneurons and GABAergic and glycinergic interneurons, all of which are excitatory at this stage of development. Recently, it has been shown that the normal pattern and frequency of this early spontaneous activity is required for appropriate motor axon path finding in the chick and for the development of cord circuits that enable appropriate flexor extensor and right-left phasing during locomotor-like activity in the mouse.

Figure 5:
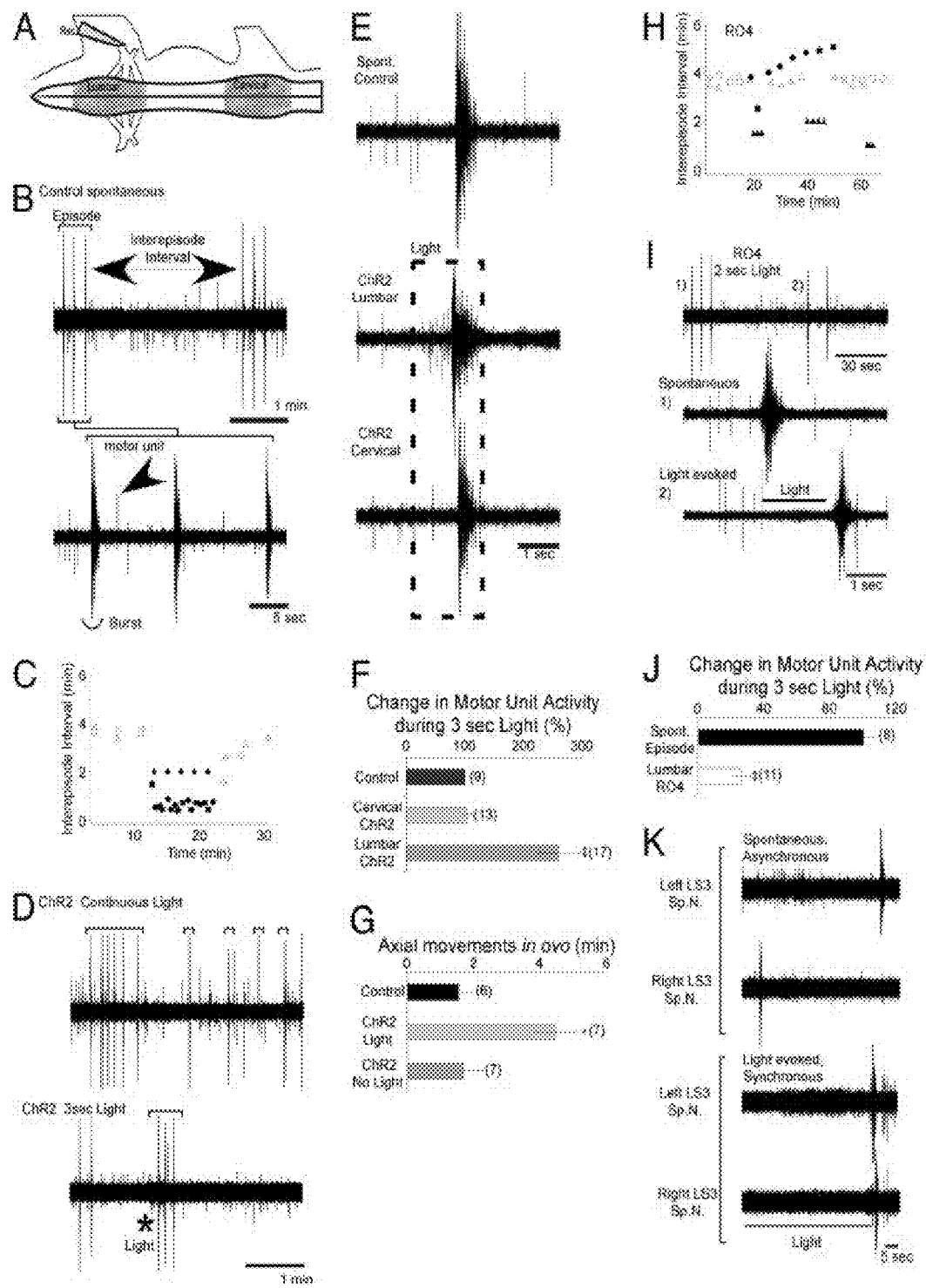
FIGS. 5(A-K) illustrate RO4 and ChR2 can be used to regulate the frequency of spontaneous rhythmic activity in isolated embryonic chick spinal cords and living embryos. (A) Diagram of isolated chicken spinal cord preparation showing the position of the recording suction electrode; regions electroporated with either ChR2 or RO4 are shown in gray. (B) Electrical recording from motor nerve of ChR2 lumbar-electroporated embryo showing two control episodes in the absence of light (Upper) with an expanded time base trace of a single episode shown (Lower). Bursts of many motor axons firing synchronously and individual motor axons firing asynchronously are noted. (C) Plot of the intervals (in min) between bursting episodes from a lumbar electroporated ChR2 embryo subjected to a long interval of continuous light (circles) or 3-s pulses of light (triangles); filled symbols indicate episodes elicited in the presence of light, and open circles indicate episodes occurring in the absence of light. (D) Electrical recordings showing episodes (denoted by brackets) occurring during several minutes of continuous light (Upper) or elicited by a 3-s pulse of light at the position of the asterisk (Lower). (E) Comparison of unit activity preceding bursts that occurred spontaneously in a nonelectroporated embryo (Top) or were elicited by light when ChR2 was expressed selectively in the lumbar cord (Middle) or cervical cord (Bottom). Time of light exposure is indicated by dashed line. (F) Bar graph of the percent change in motor unit activity occurring in control embryo and one electroporated at cervical or lumbar level during a 3-s exposure to light. (G) The frequency of axial movements of stage 25-26 embryos in ovo, 3 days after ChR2 was electroporated into cervical cord segments, in the presence or absence of 475 nM light. (H) Plot of intervals between bursting episodes in embryos electroporated with RO4 at lumbar level when exposed to a long interval of continuous light (circles) or 3-s light pulses at different repetition rates (triangles); filled symbols indicate episodes occurring in the presence of light, open symbols indicate those that occurred in the absence of light. (I) Activation of RO4 by brief light pulses triggers bursting episodes. (Top) After a spontaneous episode (no. 1) a 2-s light pulse was able to trigger a premature bursting episode (no. 2); both are shown on expanded time bases in Middle and Bottom, respectively (see text for more detail). (J) Bar graph of change in motor unit activity in the period preceding the first burst of a spontaneous episode or one evoked by light activation of RO4. (K) Light activation of RO4 can synchronize the bursting behavior of spinal cord motoneurons. Right and left sides of a RO4 lumbar electroporated cord exhibit independent (asynchronous) rhythms when they are surgically separated at the midline (top pair of traces) However, the bursts triggered after the cessation of a light stimulus results in their synchronization (bottom pair of traces). LS3, lumbar segment 3; Sp.N., spinal nerve.
Figure 8:
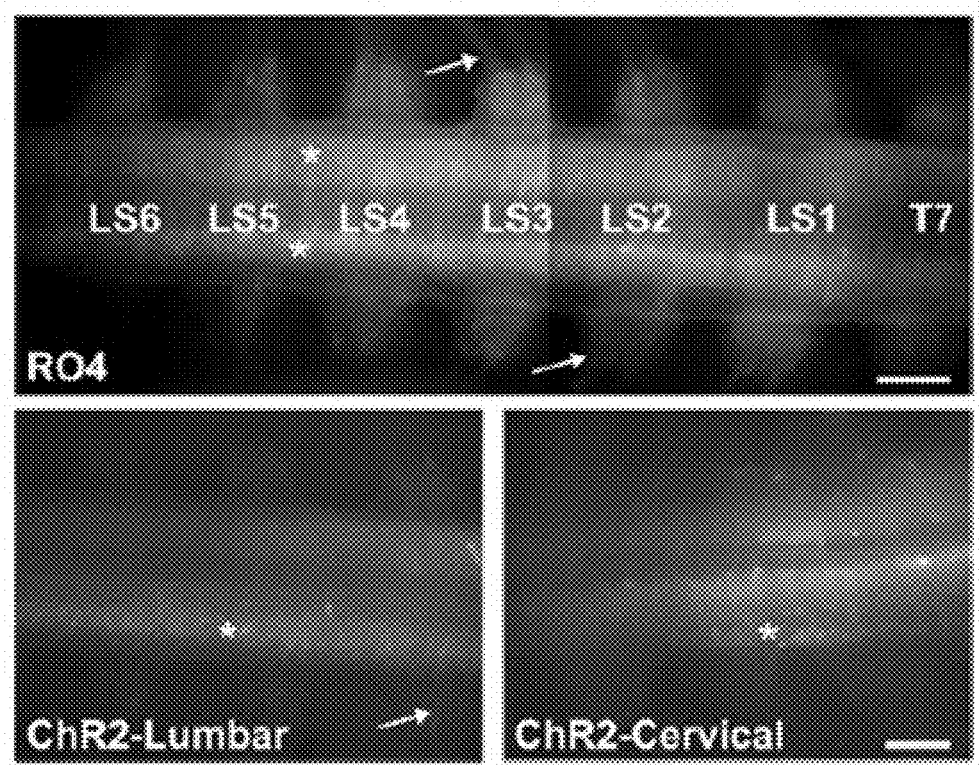
FIG. 8 illustrates expression of RO4 and ChR2 in stage 25-26 (embryonic day 4.5-5) chick spinal cords. Whole-mount spinal cord preparations are viewed from the ventral surface after a ventral laminectomy to allow visualization of cords (caudal, Left; rostral, Right). (Upper) In this example, the RO4 construct had been injected into the central canal in the lumbar region of a stage 16 (embryonic day 2.5-3) chicken embryo with the electroporation protocol described by Hanson and Landmesser (1) applied twice, with reversal of electrode polarity in between. This process resulted several days later in extensive expression of RO4 on both sides of the cord from lumbosacral segmenst (LS) 1-5. There was less strong expression in LS6 and in T(thoracic segment) 7 and no expression at other levels of the cord (data not shown). The extent of expression varied somewhat between embryos and only those with strong expression over most of the lumbosacral cord were chosen for the physiological experiments with RO4. Many motoneurons, identified by their location in the lateral motor column (asterisks) and their axons in the ventral roots, which also contained the construct (arrows), were labeled. The protocol used has been found to also label varying proportions of interneurons, identified by their location in transverse spinal cord sections (G.H., unpublished observations). Based on their locations in cord whole mounts, varying numbers of interneurons were also expressing the electroporated construct in the present experiments, although we did not attempt to quantify their proportion. The extent of the labeling depended on the age of the embryo injected and the amount of construct injected into the central canal. (Lower) ChR2 was electroporated with a similar protocol as above. However, the construct was selectively injected into either the lumbar cord (Left), where in this example its expression was higher on the embryo's right side or into the cervical cord (Right), resulting in selective expression in these regions. Asterisks indicate labeling of cells in the lateral motor column and arrows indicate labeled motor axons in the ventral roots. (Scale bar: 100 μm.)

To assess whether such network activity, especially the frequency of spontaneous bursting episodes, could be controlled noninvasively by light, constructs for GFP-ChR2 or GFP-RO4 under the control of the CMV promoter were electroporated into the spinal cords of stage 16 (embryonic day 2-3) chick embryos in ovo. At stage 26 (embryonic day 4.5-5) isolated spinal cord-hind limb preparations were made, and the constructs were found to be expressed in many neurons including motor and interneurons (FIG. 8) and could be expressed selectively in lumbar or cervical cord by varying the electroporation protocol. Suction electrode recordings from lumbar motor nerves (FIGS. 5A and B) revealed that as in control embryos the electroporated embryos exhibited episodes consisting of several bursts every 4 min (FIGS. 5B and C). Thus the electroporation protocol and expression of these constructs over several days did not appear to have any adverse effects on the development of the cord circuits responsible to generating this activity. The asynchronous firing of individual motoneurons between bursts and between episodes could also be detected (FIG. 5B, arrow). When exposed to continuous light (FIG. 5C, ●) the interepisode intervals in this cord, electroporated at the lumbar level with ChR2, were shortened to <1 min. They were, however, less rhythmic than control spontaneous episodes and consisted of single bursts (FIG. 5D Upper). In contrast, the application of a 3-s light pulse was able to elicit a normal three-burst episode shortly after a spontaneous episode (FIG. 4D Lower), and such pulses when repeated could drive episodes at precise frequencies, in the example shown (FIG. 5C, ▲) at 2-min intervals. The expanded time base traces (FIG. 5E) show that light first elicited an increase in lumbar motor unit firing that subsequently resulted in a burst very similar to spontaneous episodes in nonelectroporated embryos. However, when expression of ChR2 was restricted to the cervical cord, lumbar motor nerve recordings revealed that it was also possible to drive episodes in the lumbar cord by light without a previous increase in lumbar unit activity, by generating episodes that propagated from the cervical level (FIGS. 5E and F). Thus light, as has been previously shown for electrical stimulation, can be used to elicit episodes either by activation of local lumbar interneurons and motoneurons or activation of neurons many cord segments distant.

To assess whether light could be used to drive rhythmic activity in intact embryos in ovo, axial movements, which are precisely correlated with electrically recorded episodes of activity, were videotaped under red light that did not activate the cervically electroporated ChR2. When several light pulses of the wavelength necessary to activate ChR2 were given through a window in the shell, each elicited a clear movement episode. Furthermore, a significant increase in the frequency of axial movements could be maintained by continuous application of light over several minutes (FIG. 5G). These observations indicate that the light switches can act in intact animal preparations without application of all-trans retinal (see Discussion) and that the light used is able to penetrate through the amnion and layers of tissue to activate the spinal cord neurons.

Because light activation of RO4 hyperpolarized hippocampal neurons, we next explored whether it could be used to suppress spontaneous bursting activity. During continuous light, the interval between spontaneous episodes increased only modestly in cords with lumbar expression of RO4 (FIG. 5H, ●). This finding was not entirely unexpected because regions of cord not electroporated with RO4 would still be able to depolarize and contribute to the excitation required to elicit a bursting episode. Surprisingly, however, a 2-s pulse of light actually elicited a premature episode (5I, 2) 1 min after a spontaneous episode (FIG. 5I, 1). Yet when 1-, 1.5-, or 2-s pulses of light were given, lumbar motor unit activity was suppressed during the light and the episode was triggered only when the light was switched off (FIG. 5I, 2). During the light exposure asynchronous firing of motoneurons was also suppressed (FIG. 5I Bottom and J). Thus, while the activation of RO4 in intact cord circuits could affect excitability by the activation of other G protein-coupled pathways, for example, by activating glycine receptors that are excitatory at this stage, our results suggest that in the embroynic day 5 chick cord hyperpolarization of the transfected neurons predominates. We propose that such hyperpolarization of cells within the circuit, possibly by relieving the inactivation of voltage-gated $Na^+$ channels, enhances the probability that these cells will fire together, when the light is extinguished and thus provides another means for synchronizing bursting episodes within the circuit. Thus light activation of RO4 could precisely drive episodes at 1-, 1.5-, or 2-s intervals (FIG. 5H, ▲). In addition, when the connections between the right and left sides of the cord are surgically severed, the episodes on the two sides occur asynchronously, but can be synchronized by light activation of RO4 (FIG. 5K).

This study has shows that vertebrate rhodopsin RO4 and green algae ChR2 can be used to control neuronal function when activated by light. RO4 acted postsynaptically to hyperpolarize neurons and inhibit action potential firing and presynaptically to reduce transmitter release. We also demonstrated that ChR2 could function somato-dendritically to depolarize neurons and cause action potential firing. Whether it is transported to the presynaptic terminal where currents generated by it could modulate transmission remains to be determined. However, the transport of RO4 to presynaptic sites, where it was capable of modulating presynaptic function (transmitter release and paired-pulse facilitation), suggest that it will be a useful tool for studying G protein-mediated effects at the vertebrate presynaptic terminal in the ms time range and will provide a means for precise temporal activation and deactivation of presynaptic G proteins. Such precise activation is not possible with activating GPCRs with ligands, because washout, transport, or degradation of the ligands is slow. It is likely that ms activation of presynaptic terminal G proteins will lead to insights into the presynaptic function of G proteins, and in particular for events involved in short-term synaptic plasticity and modulation of transmitter release.

ChR2, which appears to be the protein of choice for increasing excitability and firing of neurons, was also very recently characterized in neuron. We observed that light stimulation frequencies >5 Hz led to a decrease in the success rate of action potential firing, probably because of the use-dependent decrease in ChR2 currents combined with a frequency-dependent increase in $Na^+$ channel inactivation. The 5-Hz stimulation protocol, which we found resulted in a high success rate in eliciting trains of action potentials, is in agreement with the 200-ms time it takes to recover from the ChR2-induced depolarization (FIG. 7). Thus, the extent to which a neuron will be able to precisely follow the frequency of light pulses will probably depend on the membrane properties of the different classes of neurons.

A potential concern related to the use of light-activated switches is the extent to which the light will penetrate tissues. However, we demonstrated here that the applied light was sufficient to activate both isolated spinal cords and intact embryonic day 5-6 chick embryos inside the egg, where light was applied through a window in the shell. Furthermore, the fact that light stimuli could be applied to the chick cords over many hours without altering the pattern or frequency of the spontaneous rhythmic activity in the absence of light suggests that the light has not damaged the complex cord circuits required for generating this activity. Taken together, our experiments thus demonstrate that neuronal circuits within intact embryos can be controlled by a noninvasive technique without the need for any chemical compounds.

Thus, the light switches we have developed can provide important tools for characterizing cell and network function in living animals or tissue. Placing these switches under the control of specific promoters will enable one to control the activity of specific subsets of neurons and thus determine their role in complex behaviors, as, for example, defining the roles of subclasses of interneurons and motoneurons in locomotion. Besides their utility for basic characterization of neuronal circuit function and behavior, these proteins will provide additional tools for developing externally, light-controlled molecular machines to circumvent disease or trauma-induced alterations in nervous system excitability, such as after spinal cord injuries, heart arrhythmia, and Parkinson's disease.

EXAMPLE 2

Melanopsin Variants as Intrinsic Optogenetic On and Off Switches for Transient Versus Sustained Activation of G Protein Pathways Vertebrate melanopsin (vMo) is expressed within the retina in specialized, intrinsically photosensitive retinal ganglion cells (ipRGCs), which are involved in regulating circadian rhythms. Light activation of ipRGCs in mice induces three types of $Ca^{2+}$ responses, i.e., sustained, transient and repetitive. Most likely, these $Ca^{2+}$ responses are induced via activation of different splice variants of vMos and may involve the activation of different target proteins of the Gq and other G protein pathways such as PLC, IP3 receptors and TRP channels. Studies on vMo in ipRGCs neurons suggest the activation of the Gq pathway. Expression of different vMo variants in heterologous expression systems and sequence alignments of the intracellular loop 3, which is involved in determining G protein specificity, suggest that vMo activates Gq, and to a certain extend also the Gi/o pathway.

vMo shares a greater homology with invertebrate opsins than with cone or rod opsins. It has been therefore suggested and shown that vMo functions as a multistable/bistable pigment, where regeneration/conversion of the retinal chromophores occurs within the receptor itself. Surprisingly, melanopsins as well as invertebrate opsins reveal large interspecies differences at the amino acid level. Therefore different melanopsins differ in their biophysical properties, such as wavelength dependent activation, activation and deactivation kinetics and receptor desensitization. In fact expression of human and mouse melanopsin isoforms in heterologous expression systems revealed λmax values for receptor activation between 420-480 nm.

The bistability of vMo would be ideal for optogenetic applications to switch G protein signals on and off with two different wavelengths of light. Thus, we characterized and compared the biophysical properties between the long human (huMo) and mouse melanopsin (moMo) isoforms to gain an understanding for their use and future optimization in optogenetic applications. We show that depending on the wavelength, duration and intensity of light large differences exist between huMo and moMo in their activation, deactivation and desensitization properties. While huMo is more suitable for pulsed activation, moMo is suitable for sustained activation of G protein pathways in neurons. G protein pathways can be switched on by very short, blue light pulses and switched off by yellow light, making in particular moMo an ideal and unique optogenetic tool to control G protein pathways and neuronal activity.

Material and Methods

Generation of Plasmid Constructs

The long isoforms of mouse (moMo) and human melanopsin (huMo) (GenBank accession numbers hOpn4; NM_001030015.2 and mOpn4L: NM_013887.2) were C-terminally tagged with eGFP and mCherry, respectively and inserted into NheI and SacII restriction sites of eGFP-NI and pmCherry-NI vectors with the following primer pairs: moMo forward 5'-GCT AGC ATG GAC TCT CCT TCA GGA-3' (SEQ ID NO:1) and reverse primer 5'-CCG CGG CAG ATG TCT GAG AGT CAC-3'; (SEQ ID NO:2) huMo forward: 5'-GCT AGC ACC ATG ATG AAC CCT CCT TCG GGG CCA AGA GTC CTG-3' (SEQ ID NO:3) and reverse primer 5'-CCG CGG CAT CCT GGG GTC CTG GCT GGG GAT CAG CCC-3'. (SEQ ID NO:4) To construct AAV-expression vectors, pAAV-MCS vector (Stratagene) was modified with the gateway vector conversion system (Invitrogen) as previously described Briefly, cassette A (Invitrogen) was inserted into the HincII restriction site via blunt-end ligation to create a gateway destination vector. Entry clones were generated by cloning the gene of interest into PENTR/D-TOPO shuttle vector according to manufacturer's protocol (forward primer for directional cloning into pENTR/D-TOPO with Kozak-Sequence: huMo 5'-C ACC ATG ATG AAC CCT CCT TCG GGG CCA AGA GTC CTG-3' (SEQ ID NO:5) and moMo: 5'-C ACC ATG GAC TCT CCT TCA GGA-3' (SEQ ID NO:6). The Reverse primer was created against the last codon of eGFP and mCherry, respectively (eGFP: 5'-CTA GAT ATC GGT ACC ACT AGT CTT GTA CAG CTC GTC CAT GCC GAG-3'; (SEQ ID NO:7); mCherry: 5'-CTA GAT ATC GGT ACC ACT AGT CTT GTA CAG CTC GTC CAT GCC GCC-3' (SEQ ID NO:8) LR recombination was performed to create final AAV expression clones.

Cell Culture

Human embryonic kidney 293 (HEK293) and HEK tsA 201 cells, were maintained at 37° C. in Dulbecco's modified Eagle's medium, 4.5 g 1-D-glucose, supplemented with 10% fetal bovine serum (Gibco) and penicillin/streptomycin in a humidified incubator under 5% $CO_2$. Growth medium of stable cell lines was supplemented with G418 (5 mg/ml). Stably expressing GIRK1/2 subunits HEK293 cells (kindly provided by Dr. A. Tinker UCL London, GB) were transfected with FuGENE® HD (Promega) according to the manufacturer's protocol and incubated for 18-24 h before recordings and performance of cell-based assays.

Second Messenger Assays

The fluorescent calcium sensor GCaMP6m (Addgene: plasmid #40754) was used to image Gq dependent calcium signals in HEK tsA 201 cells transiently expressing moMo, and huMo constructs cterminally tagged with mCherry. Cells were seeded into poly L-lysine coated 35 mm glass bottom dishes, co-transfected at 70% confluency with equal amounts of plasmid. DNA and used the next day. Calcium imaging was performed at an inverted Leica TCS SP5 confocal laser scanning microscope, (Leica DMI6000 B, Wetzlar, Germany) interfaced to a personal computer, running Leica Application Suite Advanced Fluorescence software (LAS AF 2.6). HEK cells were supplemented with 1 µM 9-cis retinal 1 hour before recordings. A 20x/0.7NA objective was used to acquire timelapse images (1024×512 pixels, 93 frames with 1.3 s interval for 2 min). vMos and GCaMP6 were activated with the 476 and 495 nm argon laser lines. Emission spectrum of GCaMP6 was monitored between 500 and 550 nm, Captured images were transferred into image.1 software (1.47v; NIH) and analyzed with the time series analyzer V3 plugin. Fluorescence intensity of the GCaMP6 signal was measured over time for individual cells, normalized and scaled to the maximal response amplitude. HEK cells expressing mCherry served as negative control. A luciferase-based bioluminescent assay (GloSensor™ cAMP assay, Promega) was used to detect intracellular cAMP increase as indicator for Gs activity and prepared according to the manufacturer's protocol. HEK tsA 201 cells were seeded into L-lysine coated, 96-well, black wall, clear bottom microplates (BD Biosciences). The following plasmids were co-transfected with the G1o22F plasmid(Promega): bacterial photoactivated adenylyl cyclase (bPAC, positive control), moMo-mCherry, huMo-mCherry and mCherry-NI (negative control) and incubated with 1 µM 9-cis retinal 1 hour before experiments. Luminescence measurements in combination with fluorescence excitation of photoactivated constructs were performed at room temperature in a multilable plate reader (Victor™×3, Perkin Elmer). 30 baseline luminescence measurements from three individual wells were acquired before light stimulation with 5 s delay. Light-activated proteins were excited with appropriate filter sets (bPAC: 450 nm; vMos: 485 nm) for 10 s. Luminescence increase was measured over 30 min and averaged over wells. Data was scaled to the minimum and maximum value and shown as mean±SEM.

In Vitro Electrophysiology and Data Analysis

HEK cell recordings: For GIRK channel recordings light-sensitive GPCRs were expressed in HEK293 cells stably expressing GIRK1/2 subunits. Cells were cultured and recorded in dark room conditions after transfection. GIRK-mediated K+ currents were measured and analyzed as described previously. The external solution was as follows: 20 mM NaCl, 120 mM KCl, 2 mM $CaCl_2$, 1 mM $MgCl_2$, 10 mM HEPES-KOH, pH 7.3 (KOH). Patch pipettes (2-5 megaohm) were filled with internal solution: 100 mM potassium aspartate, 40 mM KCl, 5 mM MgATP, 10 mM HEPES KOH, 5 mM NaCl, 2 mM EGTA, 2 mM MgCl2, 0.01 mM GTP, pH 7.3 (KOH). Cells were recorded in external solution containing 1 µM 9- cis retinal (Sigma) unless otherwise stated. Cells were visualized using a trans-illuminated red light (590 nm) or green light filter (480 nm) during experimental manipulations. Whole-cell patch clamp recordings of HEK293 cells were performed with an EPC9 amplifier (FIEKA). Currents were digitized at 10 kHz and filtered with the internal 10-kHz three-pole Bessel filter (filter 1) in series with a 2.9-kHz 4-pole Bessel filter (filter 2) of the EPC9 amplifier. Series resistances were partially compensated between 70 and 90%. Leak and capacitive currents were subtracted by using hyperpolarizing pulses from −60 to −70 mV with the p/4 method. The PatchMaster software (HEKA) was used for the controls of voltage and data acquisition, and off-line analysis was made with Igor Pro 6.0 software (Wavemetrics).

AAV2 Virus Production, Animals and Stereotactic Virus Injection

Recombinant adeno-associated virus stocks of serotype 8 and 9 were produced by the plasmid cotransfection method. A capsid mutant of AAV9 (AAV9.-2YF; affecting surface tyrosines) was used to produce virus particles with enhanced gene transfer efficiency and purified on an iodixanol gradient. AAV 8 stocks were prepared by the method described by Doria et al. DNase-resistant viral genomes (vg) were titered by quantitative PCR relative to standards. Titers were $9.51 \times 10^{12}$ GC/ml for AAV9.-2YF-CMV-moMo-eGFP and $1.66 \times 10^{13}$ vg/ml for AAV9.-2YF-CMV-huMo-mCherry.

For in vivo and in vitro electrophysiological experiments adult wild-type male (C57Bl/6J) mice aged 1-3 months were anesthetized with an initial dose of isoflurane and placed into a stereotaxic frame. Body temperature was controlled with a heating pad and anesthesia was maintained with 1.8-2.0% isoflurane for the entire session. To prevent corneal drying during surgery the eyes were coated with a moisturizing balm. Animals were sheared from the top of the head and the skin was opened with a sagittal incision along the midline. A burr hole was drilled for virus delivery above the cerebellar vermis (stereotactic coordinates from bregma: −6.5-7 mm anteroposterior (A/P); 0 mm mediolateral (M/L); −2000 dorsoventral (D/V)). A customized glass pipette (tip diameter about 10 μm) attached to a 10 ml syringe was used to deliver AAV solution via pressure injection in 200 μm steps starting from 2000 μm. After the surgery animals received subcutaneous injections of carprofen (2 mg/kg) for analgesia. Animals were placed individually into their homecages and allowed to recover for at least 7-14 days before performing electrophysiological experiments.

Brain Slice Recordings

Parasaggital cerebellar slices were cut from cerebellums of mice 7-21 days after AAV2 injection and recordings were performed according to Maejima et al., 2013 and. Mark et al., 2015. Briefly, mice were anesthetized with isoflurane and decapitated. The cerebellum was sliced in ice-cold artificial cerebrospinal fluid containing 125 mM NaCl, 2.5 mM KCl, 2 mM $CaCl_2$, 1 mM $MgSO_4$, 1.25 mM $NaH_2PO_4$, 26 mM $NaHCO_3$, and 20 mM glucose bubbled with 95% $O_2$ and 5% $CO_2$ using a vibratome (VT1000S, Leica) and the slices were then stored for at least 1 h at room temperature in this solution. Fluorescent mCherry or GFP-positive cells were visually identified under an upright microscope (DM-LFSA, Leica) equipped with a monochromator system (Polychrome IV, TILL Photonics) flashing excitation light (light intensity, 1 mW/mm2). Whole-cell recordings were made at room temperature in the dark except for using infrared light to target the cell. Slices were preincubated at least 20 min and continuously perfused with the external solution including 25 μM all trans-retinal, 0.025% (±)-α-tocopherol (Sigma), 0.2% essentially fatty acid free albumin from bovine serum (Sigma), and 0.1% dimethyl sulfoxide. Patch pipettes (4-8 megaohms) were filled with an internal solution with the composition 125 mM potassium gluconate, 4 mM NaCl, 2 mM MgCl2, 10 mM REYES, 0.2 mM EGTA, 4 mM Mg-ATP, 0.4 mM Na-GTP, and 10 mM Tris-phosphocreatine, pH 7.3 (KOH). Membrane currents and voltages were recorded with an EPC10/2 amplifier (HEKA). The signals were filtered at 3 kHz and digitized at 10 kHz. The PatchMaster software (HEKA) was used for the controls of voltage and data acquisition, and off-line analysis was made with Igor Pro 6.0 software (Wavemetrics).

In Vivo Extracellular Recordings and Optical Stimulation

For extracellular in vivo recordings, anaesthetized mice were placed into a stereotactic frame. Optrodes consisted of an optical fiber with 200 μm diameter (Thorlabs, FT200-UMT) fused to a customized glass-coated tungsten recording electrode (2-4 MΩ). Optrodes were coupled to a blue LED module (465 nm Plex Bright LED, Plexon) for light delivery. Light-intensity at the tip of the optrode was 1-3 $mW/mm_2$. Single- and multi-unit potentials were amplified and filtered (Gain 10 kHz; 300 Hz-10 kHz band-pass; A-M Systems, model 1800). After noise elimination (50/60 Hz Noise Eliminator, Quest Scientific) potentials were stored with a sampling rate of 20 kHz using a 1401 Power ink interface (CED), and analyzed offline using Spike2 software. One trial lasted 100 s, including 20 s baseline recordings, 10 or 60 s light stimulation, followed by additional baseline recordings. 5 trials were recorded for each cell in the 10 sec stimulation protocol and 1 trial in the 60 s stimulation protocol. Individual spikes were sorted offline either by action potential shape or individual threshold. eGFP expressing cells were used as control. Single- and multi-units were exported as Matlab files. Data analysis was done offline by a customized Matlab program. Baseline firing frequencies were determined 20 seconds before and after light stimulation, normalized and averaged over trials and cells. Peristimulus time histograms (PSTHs) were generated with Sigma Plot 12.3 software. For histology mice were deeply anesthetized with an overdose of ketamine before transcardial perfusion with 4% paraformaldehyde in 0.1 M PBS for 30 min. The brain was then removed and post fixed in paraformaldehyde for another 24 h at room temperature followed by cryoprotection in 30% sucrose (w/v) overnight at 4° C. Sagittal tissue sections (40 μm) were prepared on a cryostat and mounted on Superfrost Plus Microscope Slides and coversliped with Roti-Mount FluorCare with or without DAPI (Carl Roth). Fluorescent images were acquired at a Leica TCS SP5II confocal microscope with 10×/0.3NA, 20×/0.7NA and 40×1.1/NA objectives. Sequential z stacks were made for each section and transferred to ImageJ software (1.47v; NIH) for processing and image overlay.

Computational Two State Melanopsin Model

Figure 16A:
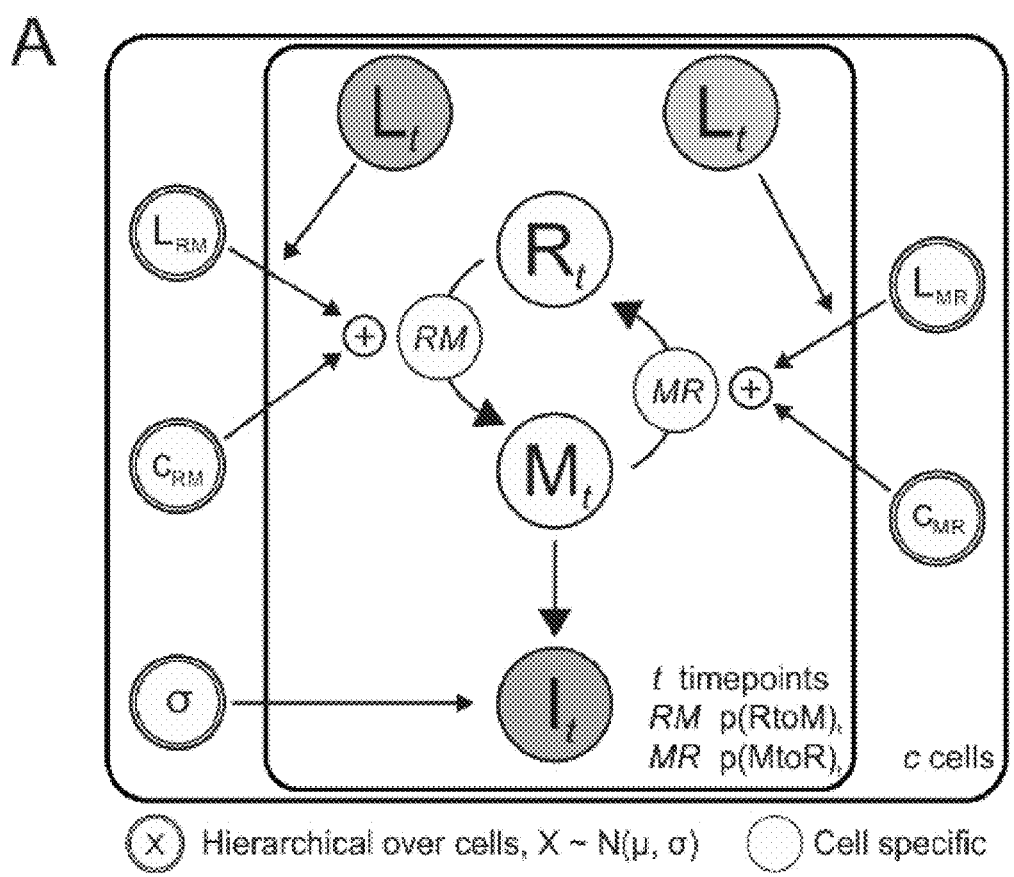
FIGS. 16(A-C) illustrate computational two state model of human and mouse melanopsin. (A) The model comprises of two states, R and M. The transition probabilities p(RtoM) and p(MtoR) are modeled by the inverse logit of a constant and a light dependent parameter (for each light source respectively). The current I is assumed to fluctuate with normal distributed noise around the M-state. Colored circle depict given data, double contour circles are the parameter to be estimated. These parameters are modeled hierarchical over cells using gaussian hyper-parameters with mean and variance. (B) Top row: baseline corrected and scaled data used to fit the model, left huMo, right moMo. Lower row: single cell median posterior estimates of the M state. The blue (470 nm) and green (560 nm) areas depict the period of light exposure. (C) The posterior parameter estimates of the model (median, 95HDI). Red depicts huMo, green moMo, blue the difference of huMo and moMo. The invlogit probabilities are defined per time step ($\Delta t=0.1$ s).

The GIRK channel recording currents were quantitatively modeled using a non-homogeneous two state hidden Markov model (FIG. 16A). The two melanopsin states R (Resting) and M (Active) were modeled with two transition probabilities (p(RtoM) and (MtoR)). The probability of occupancy of these two states always summed up to 1, they represent fractional occupancies. The transition probabilities are the sum of a time-independent factor ($C_{RM}$ and $C_{MR}$) and a light-dependent transition probability factor ($L_{RM}$ for blue activation, and $L_{MR}$ for green deactivation). The former can be interpreted as the diffusion rate to the equilibrium potential. The later are the respective time constants of decay. We combined the parameters using a logit link function to force the probabilities of the summed transition probabilities between 0 and 1. For example: $p(RtoM(i))=logitI(C_{RM}+L_{RM}*L_{blue}-on(t))$. This model is inspired by the three state model of Emanuel and Do 2015. In difference to their model, we used only two states, did not use constants defined in other experiments, but, importantly, quantitatively estimated the parameters using Bayesian parameter estimation. We combined recordings from multiple cells by adding hierarchical gaussian-hyper distributions with two parameters each to all factors. Prior to model fitting, we resampled the data to 10 Hz, baseline corrected (0 to 10 s) and then scaled to a maximal current of −1. Posterior estimates were obtained using Bayesian Hamiltonian Monte Carlo sampling (rSTAN, http://mc-stan.org/, NUTS-algorithm, with 150 warmup samples and 500 samples (4 chains, in total we analysed 1400 mcmc samples). Due to the complexity of the model we increased the maximal tree depth to 15 and the adapt-rate to 0.85. Uninformative, improper, uniform priors were used for all parameters. Rhat is a measure of between—against within—mcmcchain variance) and indicates convergence of mcmc-chains. All Rhat values were below 1.1, this is an indication (but not sufficient) for convergence. In addition, convergence was visually confirmed.

In order to model differences between huMo and moMo, we estimated the four parameters of central importance ($C_{RM}$, $C_{MR}$, $L_{RM}$, $L_{MR}$) for each species, subtracted the respective parameter chains and calculated 95% credibility intervals (quantiles). The parameter were transformed into transition probabilities per second using:

$$\text{rate}_{persecond} = 1-(1-\text{invlogit}(C_{MR}))^{fs}$$

For $L_{RM}$ and $L_{MR}$ we calculated the transition probability per second by:

$$P(L_{MR}) = 1-(1-(\text{invlogit}(C_{MR}+L_{MR})-\text{invlogit}(C_{MR}))^{fs}$$

with fs=10, the sampling rate. To estimate the explained variance we used:

$$R^2 = 1-(\text{var}(y_{raw}-M\text{-State})/\text{var}(y_{raw}))$$

The model code and analysis scripts for the model are publically available on the open science framework Statistics Statistical significance and numbers of cells and/or trials performed (n) are specified in the figure legends. For all results, the level of significance was set to p<0.05 and reported as mean±SEM. Statistical significance is indicated with "n.s." (non-significant) or asterisks with *p<0.001; p<0.01; *p<0.05.

Results

Time Course of Activation, Deactivation and Desensitization During Single and Repetitive Light Stimulation of Human and Mouse Melanopsin Expression of human melanopsin in HEK293 cells has recently revealed that vMo is capable of activating Gi/o and Gq pathways in heterologous expression systems. Since the electrophysiological characterization of the action spectrum is much more sensitive than biochemical measurements of the absorption spectrum, we made use of the possibility to activate the Gi/o pathway to characterize the biophysical properties of melanopsin variants on Gi/o mediated GIRK channel modulation. GIRK channels are modulated in a membrane-delimited, fast manner via the Gi/o pathway. We compared the amplitudes and kinetics of light-induced activation, deactivation and desensitization of GIRK channels between the human (huMo) and mouse (moMo) melanopsin when expressed in HEK293 cells stably expressing GIRK1/2 subunits.

We found that huMo and moMo induced GIRK currents during a 10 s, light pulse (470 nm; 1.8 mW/mm2) (FIGS. 9A and 9B). The activation times for both opsin variants were around 5 s (FIG. 9C). Deactivation of Gi/o induced GIRK channel activation to baseline levels only occurred when yellow light (30 s, 560 nm 1.8 mW/mm2) was applied (FIG. 9A). Complete deactivation occurred within 30 s. No differences could be observed between the activation and deactivation kinetics when either 9-cis or all-trans retinal was applied (FIG. 9A-C). However, huMo and moMo differed in the desensitization after light-stimulation and during repetitive light stimulation protocols (FIG. 10). While moMo revealed sustained GIRK currents after 10 s light stimulation for more than 5 minutes (FIGS. 10A and 10B) and could be repetitively activated without decline in response amplitude (FIG. 10D), huMo mediated light-induced GIRK current declined to less than 20% of its amplitude within one minute (FIGS. 10A and 10B). Repetitive activation (20 light pulses) also led to a 50% reduction in response amplitude (FIGS. 10D and 10E). The differences in desensitization also became obvious in the desensitization time constant, which was around 20 s for huMo but more than 60 s for moMo (FIG. 10C).

Thus, moMo reveals a sustained activation of the Gi/o protein pathway, can be repetitively activated without decline in response amplitude and can be completely switched off by yellow light. In contrast, huMo responses decline in amplitude after single and during repetitive light-stimulation.

Light Pulse Dependent Activation and Deactivation of Human and Mouse Melanopsin

Figure 11F:
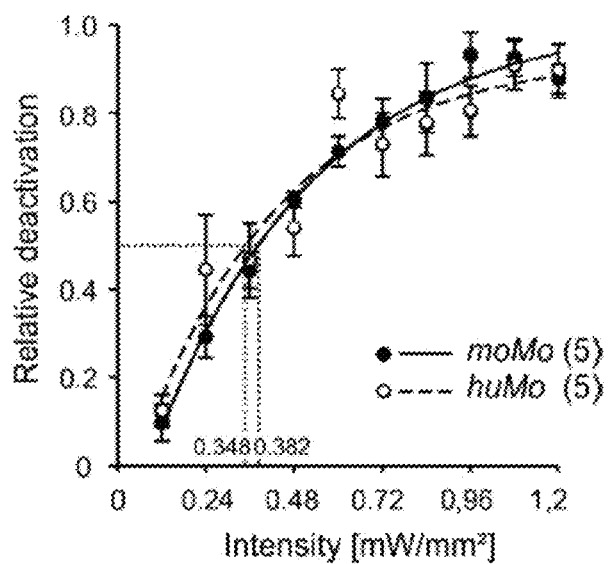
FIGS. 11(A-F) illustrate light pulse duration and light intensity dependence of GIRK currents induced by human and mouse melanopsin. (A) Comparison of light-induced GIRK currents activated by moMo and huMo using 100 ms or 10 s light pulses for activation (left) and 2 s or 10 s light pulses for deactivation (right). (B) Comparison of the light pulse duration dependence of maximal GIRK current activation induced by moMo (black) and huMo (white) using a 470 nm light pulse of the indicated duration followed by a 50 s light pulse of 560 nm. (C) Comparison of activation pulse duration time constants for the exponential fit of light pulse duration dependent GIRK current activation. (D) Comparison of the light pulse duration dependence of maximal GIRK current deactivation induced by moMo (black) and huMo (white) using a 1 s light pulse of 470 nm for GIRK current activation followed by a 560 nm light pulse of the indicated duration. (E) Comparison of the light intensity dependence of maximal GIRK current activation by moMo (black) and huMo (white) using a 10 s 470 nm light pulse for GIRK current activation of the indicated intensity followed by a 30 s 560 nm light-pulse of maximal intensity for GIRK current deactivation. (F) Comparison of the light intensity dependence of maximal GIRK current deactivation (decline of GIRK current amplitude) by moMo (black) and huMo (white) using a 10 s 470 nm light pulse of maximal intensity for GIRK current activation followed by a 30 s 560 nm light pulse of the indicated intensity for GIRK current deactivation.

We next investigated the minimal light-pulse duration for activation and deactivation of vMo mediated GIRK channel activation. We found that a 100 ms light pulse was sufficient to activate >90% of the moMo response. In contrast, a 100 ms light pulse induced only 55% of the huMo response (FIGS. 11A and 11B). For huMo a >500 ms light pulse was necessary for maximal activation of the G protein cascade. The time constant for the light pulse duration was around 40 ms for moMo and 120 ms for huMo (FIG. 11C). For the light pulse duration of the G protein deactivation we found that for huMo >80% of the G protein signal was switched off by light-pulses >2 s, while G protein deactivation for moMo needed >6 s light pulses to be switched off (FIG. 11D). The time constant for the deactivation of the light pulse was around 1 s for huMo and 5 s for moMo (FIG. 11D). Both melanopsin variants are very light sensitive since a 10 s, 0.18 mW/mm2 470 nm light pulse was sufficient to fully activate the maximal GIRK currents (FIG. 11E). In contrast, the intensity of light, where half maximal deactivation occurs, was around 0.35 mW/mm2 (FIG. 11F).

Thus, the biophysical comparison of the vMo variants reveals that moMo needs shorter blue light pulses to be switched on and longer yellow light pulses to be switched off, while huMo needs longer blue light pulses to be switched on, but shorter yellow light pulses to be switched off. The intensity of light for switching both melanopsin types on is much lower than for switching them off.

Figure 12A:
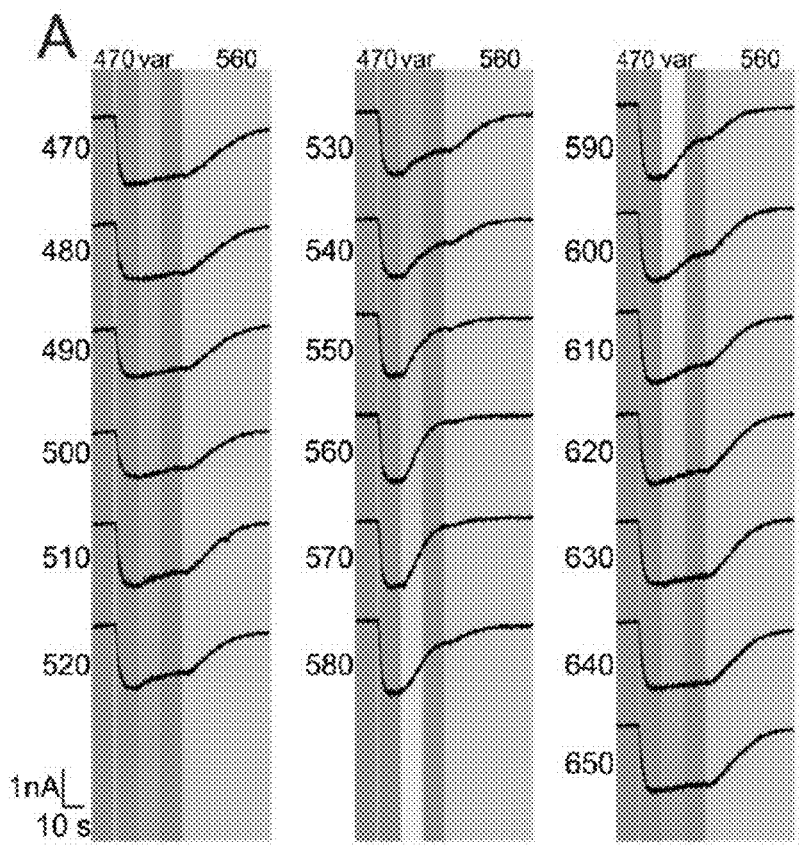
FIGS. 12(A-C) illustrate wavelength dependence of activation and deactivation of GIRK currents for human and mouse melanopsin. (A) Example traces of light-induced GIRK currents deactivated by moMo using a 10 s light pulse of the indicated wavelength. (B) Comparison of the wavelength dependence of maximal GIRK current activation induced by moMo (black) and huMo (white) using a 1 s light pulse of the indicated wavelength followed by a 40 s light pulse of 560 nm for GIRK current deactivation. (C) Comparison of the wavelength dependence of maximal GIRK current deactivation induced by moMo (black) and huMo (white) using a 1 s light pulse of 470 nm for GIRK current activation followed by a 10 s light pulse of the indicated wavelength and a 40 s light pulse of 560 nm.

Wavelength Dependence of Activation and Deactivation of Human and Mouse Melanopsin We next investigated the wavelength dependence of the activation and deactivation of vMo induced GIRK currents. We found that both moMo and huMo were maximally activated in the range between 410-470 nm (FIGS. 12A and 12B). There was an approximately 20 nm shift to longer wavelengths in the half-way light-dependent activation between huMo (50% activation at 505 nm) and moMo (50% activation at 525 nm). No or only minimal activation occurred above 550 nm for both vMo variants (FIG. 12B). In contrast to the broad activation spectrum of the vMo variants, the deactivation occurred at a narrower bandwidth. Maximal light induced deactivation occurred for both variants at around 560 nm, with no deactivation up to 490 nm. Differences between huMo and moMo could be observed at longer wavelengths of light. While no deactivation occurred for moMo at wavelengths >620 nm, the light dependent deactivation curve was much broader for huMo (FIG. 12C).

Thus, both vMo variants can be sufficiently activated by light pulses between 400-480 nm and deactivated by light pulses between 540-580 nm.

Figure 13C:
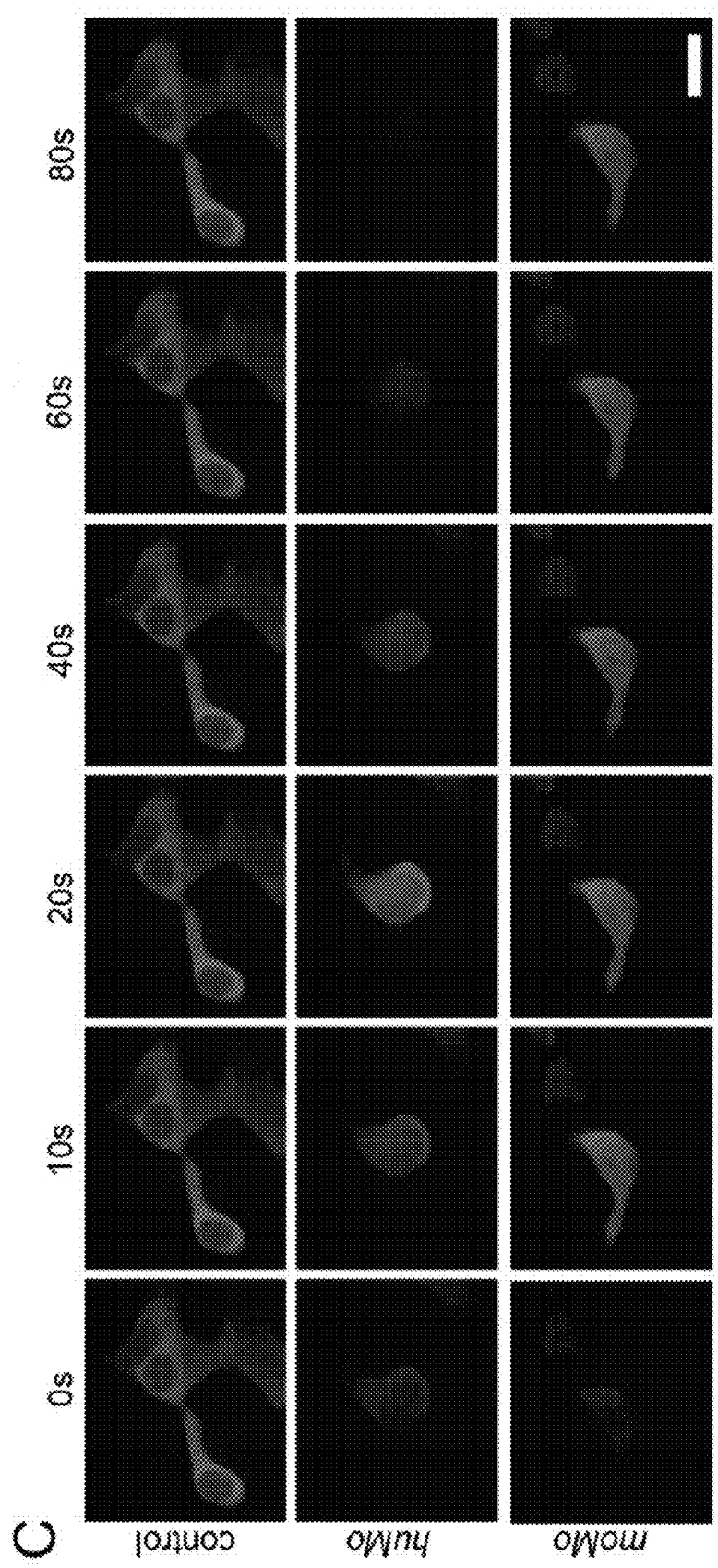
FIGS. 13(A-C) illustrate light-induced changes in intracellular Ca2+ levels by human and mouse melanopsin. (A) Representative photomicrographs showing transient expression of control vectors (upper panel) eGFP-NI (green) and mCherry-NI (red) together with melanopsin fusion proteins (lower panel) moMoeGFP (green) and huMo-mCherry (red). Melanopsin fusion proteins show membrane associated trafficking compared to cytoplasmic expression of control vectors; scale bar: 20 μM. (B) moMo and huMo induced normalized calcium responses measured with GCaMP6 differ in their response kinetics. Light-activation of moMo induces sustained $Ca^{2+}$ responses, while light activation of huMo induces a $Ca^{2+}$ signal, which immediately declines in amplitude. Cells expressing mCherry (control) show now increase in baseline fluorescence level upon light stimulation. (C) Confocal images showing time-lapse recordings of transfected HEK cells expressing GCaMP6 cotransfected with mCherry-NI (control), moMo-mCherry or huMo-mCherry at different time points and 470/495 nm light-stimulation. Numbers in parenthesis indicate the number of wells; scale bar: 20 μM; values are given as mean±SEM. Note, huMo and moMo do not activate the Gs pathway (see FIG. 17).
Figure 17:
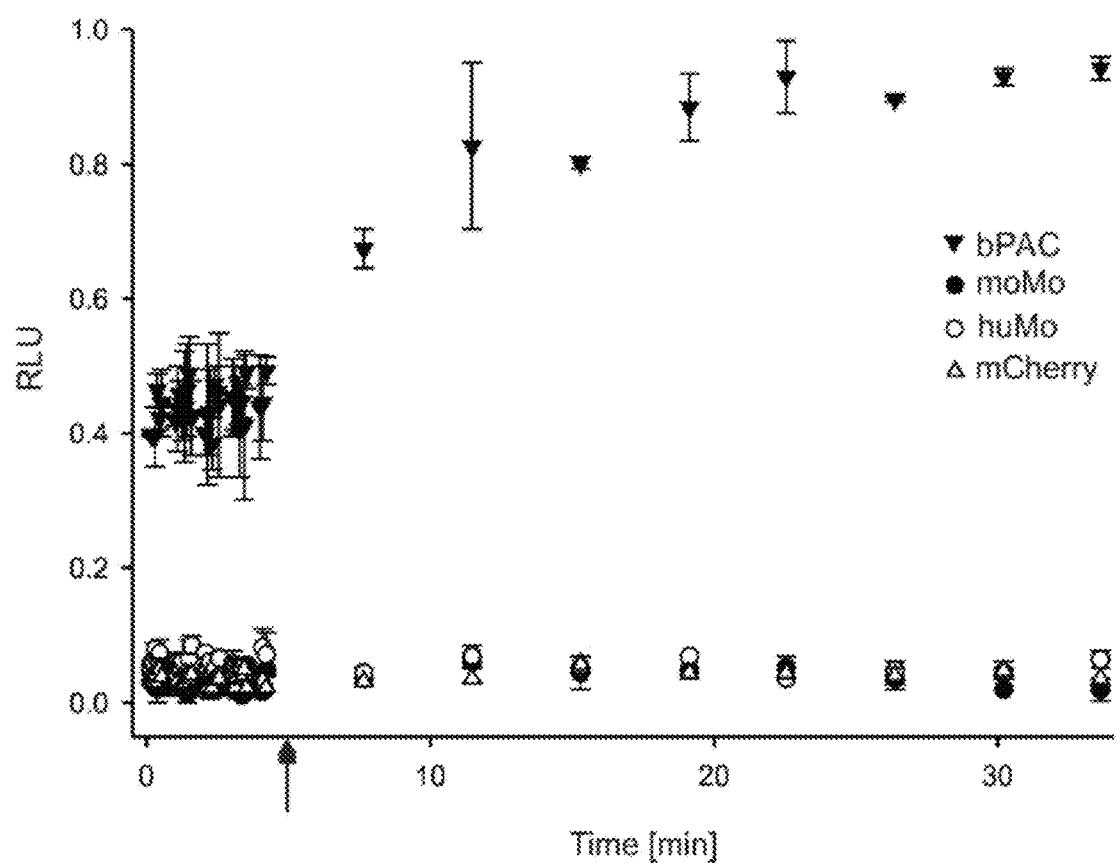
FIG. 17 illustrates cAMP dependent Gs activity in HEK 293 cells expressing bPAC and human and mouse melanopsin reveal that the melanopsin variants do not activate the Gs pathway. A bioluminescent sensor was used to monitor changes in cAMP production following light-induced activation of the Gs pathway. After 30 baseline luminescence measurements without light stimulation, blue light (485 nm) was used (black arrow indicates onset of light stimulation) for light-dependent Gs activation. Blue light triggered cAMP production in cells expressing bPAC but not those expressing vMos or mCherry (n=3 wells). RLU, relative luminescence units; values are given as mean±SEM.

Light Dependence of Activation of the Gq Pathway By Human and Mouse Melanopsin in HEK293 Cells Since melanopsin couples mainly and/or exclusively to the Gq pathway in ipRGCs, we next investigated the light-dependent activation of the Gq/11 pathway using moMo and huMo. We monitored the Gq/11 induced rise in intracellular Ca2+ using GCaMP6 in HEK293 cells. We found that light-activation of moMo induced a robust sustained Ca2+ signal, while light activation of huMo induced a Ca2+ signal, which immediately declined in amplitude (FIGS. 13B and 13C). The time constant for the decline in Ca2+ responses for huMo was 15 s, while the change in fluorescence over time for moMo resembled the GCaMP6 control (FIGS. 13B and 13C). GCaMP6 and vMos are both activated by blue light. Therefore, we did not try to deactivate vMos with 560 nm light, since monitoring GCaMP6 would always activate vMos. Since vMos are capable to interact with different G protein partners we also tested Gs activation (FIG. 17). We could not detect measurable cAMP-dependent Gs activation in any of the vMo variants compared with light-dependent increase in luminescence with bPAC expressing cells (FIG. 17).

Thus, the Gq/11 mediated Ca2+ response curves of moMo and huMo resemble the Gi/o mediated GIRK channel activation, i.e., moMo induces sustained pathway activation, while huMo responses decrease over time.

Figure 14A:
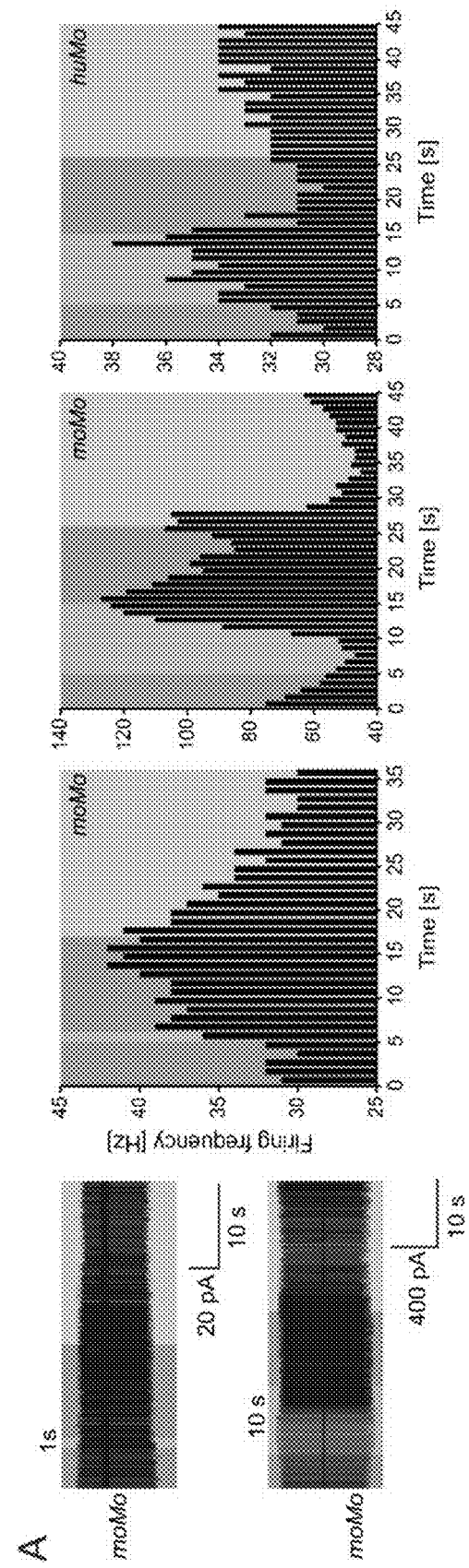
FIGS. 14(A-D) illustrate light dependent activation and deactivation of cerebellar Purkinje cells by human and mouse melanopsin. (A) Example traces of light-induced modulation of PC firing in cerebellar slices by moMo using 1 s or 10 s, 470 nm light-pulses for sustained increase in firing frequency, followed by a dark-phase of 11 s and a 19 s, 560 nm light-pulse for termination (left). Corresponding PSTHs (bin size 1 s) compared to transient increase in firing frequency during 10 s 470 nm light-pulses by huMo (right). (B) Comparison of relative change in normalized firing frequency by moMo and huMo for all recorded cells. 45 s stimulation period was divided into four blocks and analyzed individually: pre, 5 s darkphase; blue, 10 s, 470 nm light-pulse; dark, 11 s dark-phase, green, 19 s, 560 nm light-pulse. Firing frequency is sustainably increased by moMo using 470 nm light-pulses and can be significantly decreased using light-pulses of 560 nm. In contrast, light induced increase in firing frequency by huMo is transient and significantly decreases during dark-phase. (C) Example traces of current influx induced by moMo (top) and huMo (bottom) using 10 s, 470 nm light pulses. Current influx is maintained during dark phase and can be switched off by 560 nm lightpulses for moMo, whereas huMo induced current influx declines to baseline levels during darkphase. (D) Comparison of current amplitudes activated by huMo and moMo using 10/19 s light-pulses of 470/560 nm.

Optogenetic Performance of moMo and huMo in Brain Slices: Light Dependent Activation and Deactivation of Cerebellar Purkinje Cells We next investigated if the vMo variants can be used to switch neurons on and off using two different wavelengths of light. We therefore expressed moMo and huMo in cerebellar Purkinje cells (PCs) and analyzed the firing properties and membrane conductance before, and during blue and yellow light stimulation in cerebellar slices (FIG. 14). PCs reveal an intrinsic firing activity, which can be modulated for example by excitatory, glutamatergic input involving GPCRs coupling to the Gq/11 pathway. We found that a 1 s long, blue light pulse was sufficient to increase PC firing sustainably (FIG. 9A). Continuous firing persisted after light was switched off without any significant decline in firing frequency (FIGS. 14A and 14B). A 20 s long, yellow light pulse significantly decreased AP firing close to baseline frequencies (FIGS. 14A and 14B). With a 10 s blue light pulse we were even able to counteract the intrinsic decline in firing frequency (FIGS. 14A bottom and 14B). In contrast, light activation of huMo increased the AP firing frequency transiently. Firing frequencies showed a significant decline after blue light application (FIGS. 6A and 6B). AP firing can be elicited via influx of cations into neurons. Therefore we investigated if activation of vMo is activating an inward current and if this current can be switched on and off by blue and yellow light. Using whole cell voltage clamp recordings of PCs, we found that blue light activation of moMo induced a current influx, which was maintained in the dark and could be switched off by yellow light (FIGS. 14C and 14D). Again, activation of huMo induced a transient inward current, which declined to baseline levels after light was switched off. Both vMos showed no significant difference in light induced current amplitude (FIG. 14D).

Thus, moMo can be used to switch PCs on and off using two different wavelengths of light. In contrast, huMo can be used to transiently modulate the firing activity of PCs.

Figure 15H:
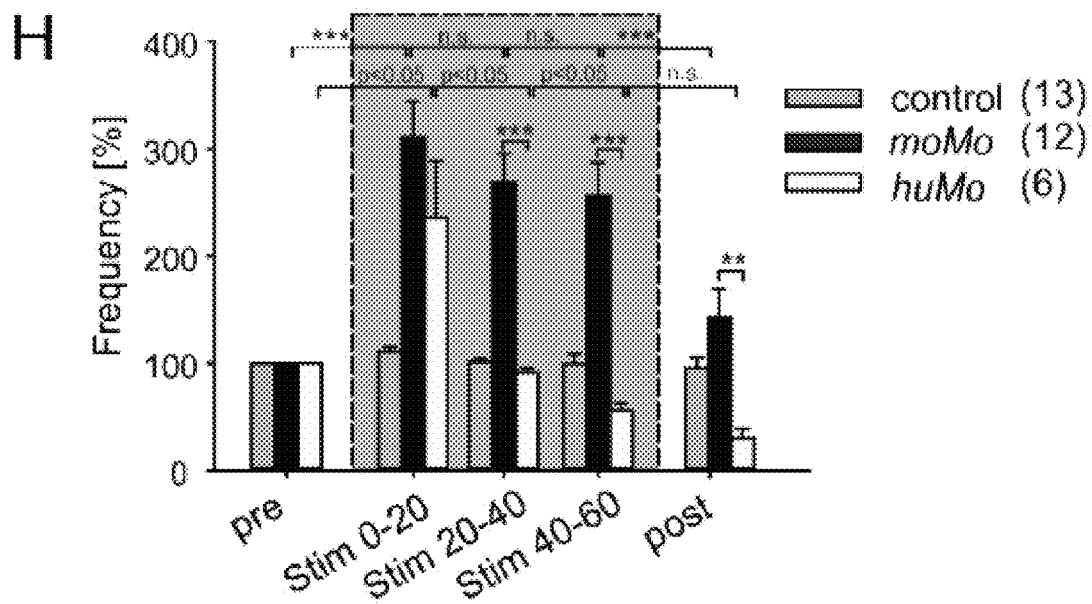
FIGS. 15(A-H) illustrate sustained and transient modulation of neuronal firing in the cerebellum in vivo induced by light-dependent activation of mouse and human melanopsin. (A-B) Confocal images from brain sections of the cerebellar cortex expressing AAV9.-2YF-CMVmoMo-eGFP (A) and AAV9.-2YF-CMV-huMo-mCherry (B) in apical dendrites, axon terminals and around the soma of cerebellar Purkinje cells; scale bars (A): 200 μM; 100 μM; 20 μM; scale bars (B):200 μM; 100 μM; 50 μM. (C) Example traces of in vivo optrode recordings from anaesthetized mice show sustained activation of neuronal activity after moMo-eGFP stimulation with a 10 s light pulse and corresponding PSTH (bin size 1 s) compared with control (below). (D) Light-induced increase in firing frequency with moMo-eGFP sustains after termination of light compared with control. *p<0.05 RM ANOVA on ranks with SNK post hoc analysis; ***p<0.001 Mann-Whitney Rank Sum test. (E-G) Example traces and corresponding PSTHs (bin size 1 s) from cerebellar cortex from in vivo optrode recordings in anaesthetized mice. Neurons expressing moMo-eGFP (E), huMo-mCherry (F) and GFP (control) show different activation pattern after sustained light stimulation (blue bar, 60s). (H) Average increase of normalized firing frequency for all recorded cells. 60 s stimulation period was divided into three blocks of 20 s ($1^{st}$ block: 0-20 s; 2nd block: 20-40 s; 3rd block: 40-60 s) and analyzed individually. Dashed line marks the light stimulation interval. moMo-eGFP constantly increases firing frequency over the total stimulation period without significant reduction over the entire stimulation period. In contrast, light induced increase in firing frequency following huMo-mCherry stimulation significantly declines after the first stimulation period. No significant change in firing frequency was observed in control cells expressing GFP. *p<0.05 RM ANOVA on ranks with SNK post hoc analysis, p<0.01 Mann-witney Rank Sum test, *p<0.01 RM ANOVA with Bonferroni post hoc analysis for within subject comparison and Mann-Whitney Rank Sum test for between subject comparison. Blue boxes: light stimulation using 465 nm light; gray boxes: dark phase without light stimulation; values are shown as mean±SEM; numbers in parenthesis indicate number of trials in D and number of recorded cells in H.

Optogenetic Performance of moMo and huMo In Vivo: Sustained vs. Transient Control of Purkinje Cell Firing We next investigated if we can use vMo variants to induce transient or sustained modulation of PC firing in vivo. PCs were infected using an adeno-associated viral vector serotype for AAV9.-2YF under the control of the CMV promoter (FIGS. 15A and 15B) in experimental animals. Control animals matched for age, incubation time, and illumination parameters received a viral vector carrying the fluorophore alone (AAV8-CMV-eGFP). We found that a 10 s long blue light pulse was sufficient to induce sustained increase in PC firing in moMo expressing PCs (FIG. 15C) even after light was switched off (FIGS. 15C, and 15D). Sustained increase in PC firing was also observed during a 60 s continuous light pulse (FIGS. 15E and 15H). In contrast, light activation of huMo expressing PCs (FIG. 15B) led to a rapid, transient increase in PC firing, which declined to baseline levels within 60 s (FIGS. 15F and 15H).

Thus, moMo and huMo can be used to induce sustained or transient activation of G protein pathways and modulation of neuronal targets.

Computational Model of Activation and Deactivation

In order to gain an understanding of how bistability can be influenced by different parameters leading to sustained or transient responses we developed a generative model of normalized melanopsin GIRK currents (FIG. 16) and estimated its parameters based on the data shown in FIG. 9. It is formulated within the framework of hidden markov models with two hidden states. The transition probabilities (p(RtoM) and p(MtoR)) between the two states, the resting (R-State) and the active state of melanopsin (M-State) are modulated by light. Thus, this model disentangles the constant transition probabilities ($C_{RM}$ and $C_{MR}$) that return the cell to an equilibrium state, from the influence of 470 nm ($L_{RM}$) and 560 nm light ($L_{MR}$).

We estimated the parameters of the model using Bayesian Markov Chain Monte Carlo Posterior sampling. We evaluated the goodness of fit, by the proportion of explained variance between the single cell posterior predictions of the M-state and the raw data: $R^2$ is 0.98 with a Bayesian 95% credibility interval of [0.94, 0.99]. In fact, we additionally account for the stochastic part of the variance resulting from measurement noise (over cells: σ=0.06 [0.05, 0.08]), thus improving on this value. The estimated parameters can be interpreted (with a transformation, see Methods) as transition probabilities. The constant change from resting to active state ($C_{RM\ is}$ 7200 e-6/s [670 e-6/s, 65000 e-6/s] in huMo and 330 e-6/s [3,2 e-6/s , 4400 e-6/s] in moMo. We presently do not have definitive evidence to state that the two species differ in this aspect (in logit scale: 3.1 [−0.34, 8]), but the likelihood is high (with 97% certainty) that huMo has a higher transition probability $C_{RM}$. The constant transition probability from M to R ($C_{MR}$) is estimated higher, with 47000 e-6/s [33000 e-6/s, 70000 e-6/s] in huMo, than 7200 e-6/s [3800 e-6/s, 13000 e-6/s] in moMo, with a statistically significant difference (in logit scale) of 1.9 [1.2, 2.7].

Blue light stimulation leads to an activation of melanopsin. This is reflected in the additional transition probability of 330000 e-6/s [22000, 999000 e-6/s] for ($L_{RM}$) in huMo, and 997000 e-6/s [140000 e-6/s, 1000000 e-6/s] in moMo, with a difference (in logit scale) of −2.8 [−7.8, 0.91]. The results suggest (with 94% certainty), that the change in transition probability for blue light is faster in moMo in comparison to huMo. For a deactivation through green light ($L_{RM}$), we estimated 270000 e-6/s [65000 e-6/s, 770000 e-6/s] for huMo and 480000 e-6/s [280000 e-6/s, 720000 e-6/s] for moMo, suggesting that the evidence for a difference is weak (84% certainty, difference on logit scale: −0.66 [−2, 0.91]).

Thus, by using a simple model with two hidden states and four parameters, we are able to adequately describe the biophysical differences between moMo and huMo and precisely estimate its underlying parameters necessary for sustained or transient activation of G protein signaling cascades.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A light-sensitive G-protein coupled receptor comprising:
   a light sensitive extracellular melanopsin domain, the intracellular domain corresponding to at least a portion of the 5HT receptor domain effective to modulate serotonergic signaling, and a heterologous intracellular domain capable of modulating an intracellular signaling pathway, the melanopsin domain comprising a native vertebrate melanopsin (vMo) amino acid sequence.

2. The light-sensitive G-protein coupled receptor of claim 1, the melanopsin selected from the group consisting of human melanopsin (huMo) and mouse melanopsin (moMo).

3. The light-sensitive G-protein coupled receptor of claim 2, the melanopsin comprising a long mouse melanopsin (mOpn4L).

4. The light-sensitive G-protein coupled receptor of claim 1, the intracellular domain coupling a G-protein subunit to affect at least one G-protein pathway selected from group of Gi, Gq, and Gs.

5. The light-sensitive G-protein coupled receptor of claim 1, the intracellular domain comprising an amino acid sequence corresponding to an amino acid sequence of at least one 5HT intracellular loop selected from the group consisting of a 5HT-2A loop, a 5HT-1A loop, and a 5HT-4A loop.

6. A light-sensitive G-protein coupled receptor comprising:
   a light sensitive extracellular melanopsin domain, the melanopsin domain comprising an amino acid sequence corresponding to a native vertebrate melanopsin (vMo) wherein the melanopsin EF loop amino acid sequence is replaced by a heterologous GPCR EP loop amino acid sequence, and
   a heterologous intracellular domain capable of modulating an intracellular signaling pathway the intracellular domain corresponding to at least a portion of the 5HT receptor domain effective to modulate serotonergic signaling.

7. The light-sensitive G-protein coupled receptor of claim 6, the melanopsin selected from the group consisting of human melanopsin (huMo) and mouse melanopsin (moMo).

8. The light-sensitive G-protein coupled receptor of claim 7, the melanopsin comprising a long mouse melanopsin (mOpn4L).

9. The light-sensitive G-protein coupled receptor of claim 6, the intracellular domain coupling a G-protein subunit to affect at least one G-protein pathway selected from group of Gi, Gq, and Gs.

10. The light-sensitive G-protein coupled receptor of claim 6, the intracellular domain comprising an amino acid sequence corresponding to an amino acid sequence of at least one 5HT intracellular loop selected from the group consisting of a 5HT-2A loop, a 5HT-1A loop, and a 5HT-4A loop.

* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1
gctagcatgg actctccttc agga                                           24

<210> SEQ ID NO 2
<211> LENGTH: 24
<212> TYPE: DNA
<213> ORGANISM: Artificial Sequence
<220> FEATURE:
<223> OTHER INFORMATION: Synthetic Construct

<400> SEQUENCE: 2
ccgcggcaga tgtctgagag tcac                                           24

<210> SEQ ID NO 3
<211> LENGTH: 42
<212> TYPE: DNA
<213> ORGANISM: Artificial Sequence
<220> FEATURE:
<223> OTHER INFORMATION: Synthetic Construct

<400> SEQUENCE: 3
gctagcacca tgatgaaccc tccttcgggg ccaagagtcc tg                       42

<210> SEQ ID NO 4
<211> LENGTH: 36
<212> TYPE: DNA
<213> ORGANISM: Artificial Sequence
<220> FEATURE:
<223> OTHER INFORMATION: Synthetic Construct

<400> SEQUENCE: 4
ccgcggcatc ctggggtcct ggctggggat cagccc                              36

<210> SEQ ID NO 5
<211> LENGTH: 37
<212> TYPE: DNA
<213> ORGANISM: Artificial Sequence
<220> FEATURE:
<223> OTHER INFORMATION: Synthetic Construct

<400> SEQUENCE: 5
caccatgatg aaccctcctt cggggccaag agtcctg                             37

<210> SEQ ID NO 6
<211> LENGTH: 22
<212> TYPE: DNA

```
<213> ORGANISM: Artificial Sequence
<220> FEATURE:
<223> OTHER INFORMATION: Synthetic Construct

<400> SEQUENCE: 6
caccatggac tctccttcag ga                                              22

<210> SEQ ID NO 7
<211> LENGTH: 45
<212> TYPE: DNA
<213> ORGANISM: Artificial Sequence
<220> FEATURE:
<223> OTHER INFORMATION: Synthetic Construct

<400> SEQUENCE: 7
ctagatatcg gtaccactag tcttgtacag ctcgtccatg ccgag                     45

<210> SEQ ID NO 8
<211> LENGTH: 45
<212> TYPE: DNA
<213> ORGANISM: Artificial Sequence
<220> FEATURE:
<223> OTHER INFORMATION: Synthetic Construct

<400> SEQUENCE: 8
ctagatatcg gtaccactag tcttgtacag ctcgtccatg ccgcc                     45
```